United States Patent
Johannesson et al.

(10) Patent No.: US 12,046,362 B2
(45) Date of Patent: Jul. 23, 2024

(54) OPERATING A MEDICAL DEVICE DURING STARTUP AND SHUTDOWN

(71) Applicant: GAMBRO LUNDIA AB, Lund (SE)

(72) Inventors: Camilla Johannesson, Lomma (SE); Mikael Lindhult, Lund (SE); Niklas Mebius, Bunkeflostrand (SE)

(73) Assignee: Gambro Lundia AB, Lund (SE)

( * ) Notice: Subject to any disclaimer, the term of this patent is extended or adjusted under 35 U.S.C. 154(b) by 653 days.

(21) Appl. No.: 17/282,965

(22) PCT Filed: Oct. 10, 2019

(86) PCT No.: PCT/EP2019/077428
§ 371 (c)(1),
(2) Date: Apr. 5, 2021

(87) PCT Pub. No.: WO2020/074618
PCT Pub. Date: Apr. 16, 2020

(65) Prior Publication Data
US 2021/0391068 A1    Dec. 16, 2021

(30) Foreign Application Priority Data

Oct. 10, 2018 (EP) ..................................... 18199665

(51) Int. Cl.
G16H 40/40    (2018.01)
(52) U.S. Cl.
CPC .................................. *G16H 40/40* (2018.01)
(58) Field of Classification Search
CPC ...................................................... G16H 40/40
See application file for complete search history.

(56) References Cited

U.S. PATENT DOCUMENTS 9,804,836 B2 * 10/2017 Gondek ................. G16H 40/63
10,201,714 B2    2/2019 Delisle et al.
(Continued)

OTHER PUBLICATIONS

International Search Report from corresponding International Patent Application No. PCT/EP2019/077428, mailed Feb. 4, 2020.

*Primary Examiner* — Manuel A Rivera Vargas
(74) *Attorney, Agent, or Firm* — K&L Gates LLP

(57) ABSTRACT

A medical device comprises a software (SW) system for execution by processor(s). The SW system defines a plurality of subsystems, including a primary subsystem and one or more secondary subsystems, and each subsystem comprises SW applications involved in the operation of the medical device during a medical procedure. A deterministic and distributed startup of the SW system is enabled by separating the startup procedure into a preparation for startup on a subsystem level, by use of two different notifications, and a preparation for startup on a system level, in which the primary subsystem coordinates startup of the subsystems. The method comprises: initiating (401) each SW application; providing (402), by each SW application in the respective secondary subsystem when ready for startup, an "application ready" notification; providing (403), by the respective secondary subsystem when all of its SW applications have provided the "application ready" notification, a "subsystem ready" notification; and coordinating (405), by the primary subsystem upon receiving the "subsystem ready" notification, startup of the subsystems.

22 Claims, 10 Drawing Sheets

(56) References Cited

U.S. PATENT DOCUMENTS

| | | | |
|---|---|---|---|
| 2003/0135389 A1 | 7/2003 | Gudapakkam et al. | |
| 2014/0121509 A1* | 5/2014 | Mansker | G16H 40/40 |
| | | | 600/407 |
| 2017/0024220 A1* | 1/2017 | Grimme | G06F 9/442 |
| 2017/0246466 A1 | 8/2017 | Murphy et al. | |

* cited by examiner

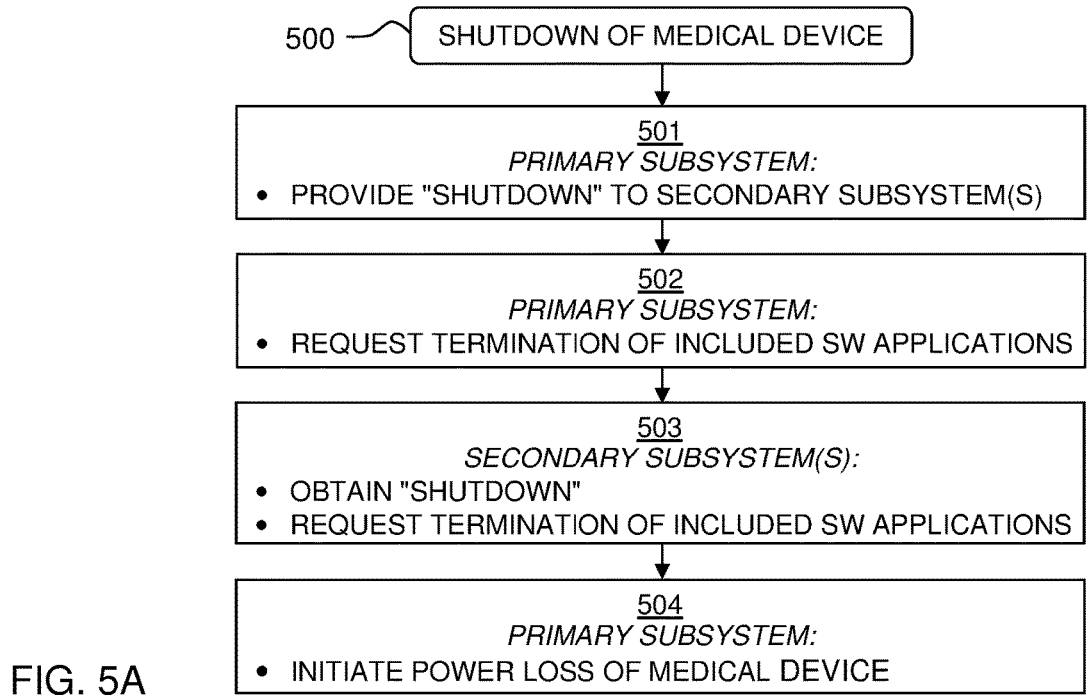
FIG. 5A
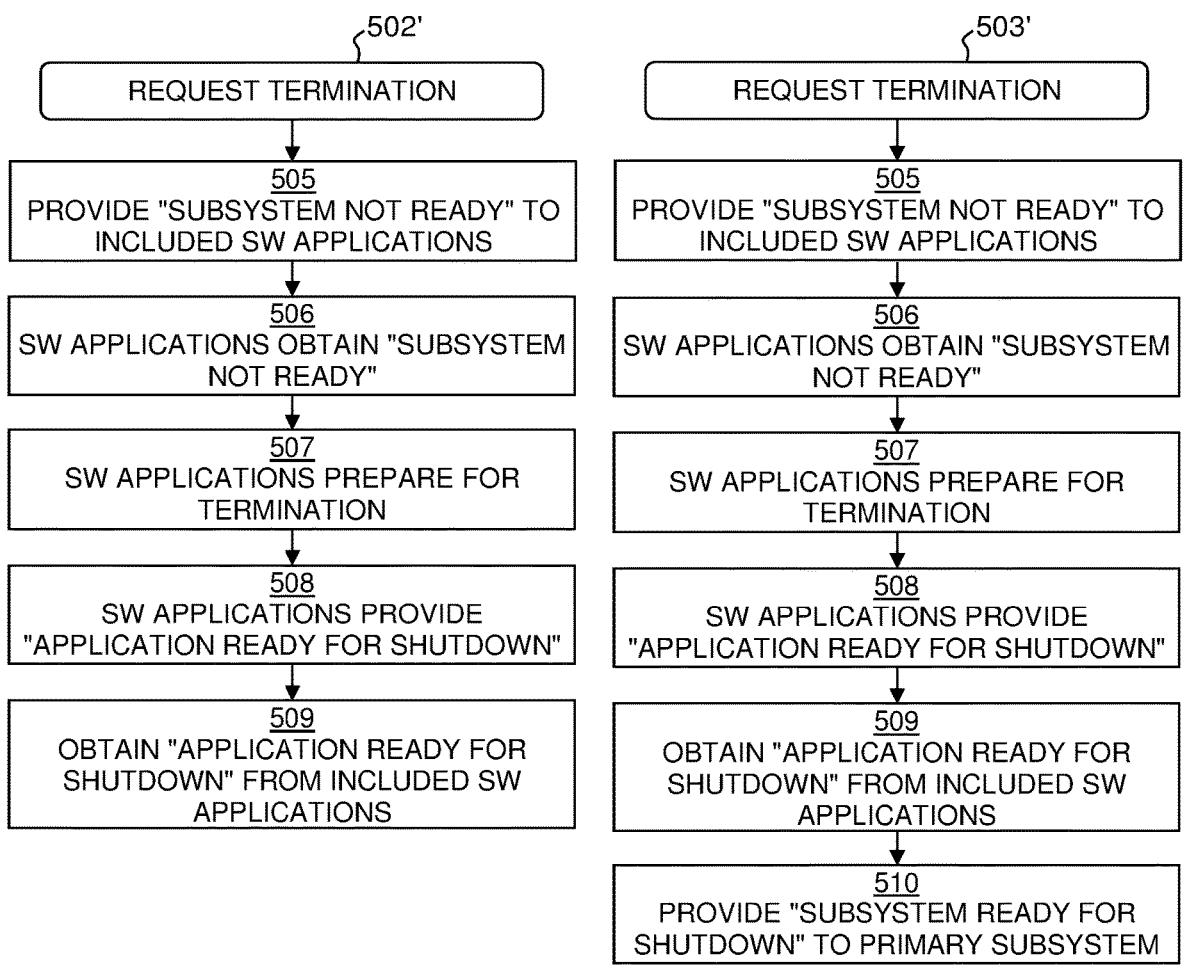
FIG. 5B
FIG. 5C

OPERATING A MEDICAL DEVICE DURING STARTUP AND SHUTDOWN

PRIORITY CLAIM

The present application is a National Phase of International Application No. PCT/EP2019/077428, filed Oct. 10, 2019, which claims priority to EP Application No. 18199665.3, filed Oct. 10, 2018. The entire contents of each are incorporated herein by reference and relied upon.

TECHNICAL FIELD

The present invention relates to the field of medical devices, and more specifically to techniques for operating automated medical devices during startup and shutdown.

BACKGROUND ART

An automated medical device is a machine, whether used alone or in combination, intended by the manufacturer to be used for humans or animals for a medical purpose. Such a purpose may include diagnosis, prevention, monitoring, treatment or alleviation of a disease, injury, or handicap.

Automated medical devices are frequently used in the health care sector and are subject to strict regulatory frameworks to ensure that they are safe and efficient.

In general, an automated medical device is operated by a software system, which is a complex system that needs to be carefully designed so as to mitigate the risk of malfunctions that may have health implications.

It may be desirable to design the software system to be composed of two or more independent subsystems or modules. Constructing a suite of independent subsystems affords product designers and manufacturers of the medical device the ability to create and deploy subsystems that perform specific functions that are a subset of the functions of the complete medical device. Such a modularization of software may also be paired with a modularization of hardware, by different subsystems being executed on different processors, e.g. located on one or more integrated circuits or chips.

Although much effort typically is put into designing the software system to ensure that the medical device operates in a controlled, safe and reliable manner while performing the medical purpose, startup and shutdown of the medical device is often neglected and performed by presuming nominal startup times for individual processes and using corresponding timers. This may lead to long startup times and is prone to malfunction if a process startup should be delayed, for any reason, beyond the nominal startup time. Malfunctions occurring during startup or shutdown may have serious impact on the subsequent medical procedure performed by the medical device, regardless of safety measures built into the software system. Startup and shutdown may be particularly vulnerable to malfunction in software systems that are modularized into two or more subsystems.

There is a general need to provide a software system for a medical device that ensures a deterministic, safe and reliable startup and shutdown of the medical device.

The prior art comprises the article "Logical Architecture of Medical Telediagnostic Robotic System", by Stanczyk et al, published in 21st International Conference on Methods and Models in Automation and Robotics (MMAR), pages 200-205 (2016). The article presents a multifunctional robotic system which allows for remote physical examination. A patient-side control system comprises a robot central control system (RCCS) which is connected to lower-level components, e.g. lower-level control devices for a robot head, a robot arm and a mobile robot base, respectively. Based on sensor signals, logical demands of assistant or doctor, and status signals from all lower-level components, RCCS makes decisions whether the lower-level components may be operated or not. All communication goes through the RCCS. When power on is enabled, RCCS goes to a startup state to initiate a startup procedure. When all lower-level components are recognized as active, RCCS goes to an active state. Conversely, when a power off button is pushed, RCCS goes to a shutdown state to start a shutdown procedure. When all lower-level components finish shutdown procedures, RCCS goes to an off state.

Although such a prior art control system may enable safe and reliable startup of the hardware components of the robotic system on a high-level, it does not ensure a deterministic startup of all processes of the control system.

The prior art also comprises US2014/0121509, which discloses a dependency-based startup method in a multi-modality medical processing system. A system controller is arranged to coordinate startup and shutdown of a plurality of executable components, which are modality-specific components for communication with a respective medical device coupled to the processing system. For each executable component, the system controller acquires dependency information that includes a list of other executable components upon which the executable component depends. The system controller dynamically derives a start order for the plurality of executable components based on the dependency information and starts the executable components according to the start order. The system controller waits until the respective component has published all of its interfaces, and optionally has broadcast a process ready message, before starting the next component in the start order.

This startup method only considers startup on the level of executable components. Thereby, it does not ensure a deterministic startup of all processes in the system, e.g. processes performed by software applications within one or more of the executable components. Further, the proposed startup method is complex in that it requires exchange of dependency information and a centralized determination of a start order by the system controller.

SUMMARY

It is an objective of the invention to at least partly overcome one or more limitations of the prior art.

A further objective is to enable a deterministic startup of all relevant processes of a software system for operating a medical device.

Another objective is to enable a deterministic shutdown of all relevant processes of a software system for operating a medical device.

One or more of these objectives, as well as further objectives that may appear from the description below, are at least partly achieved by a method of operating a medical device, a medical device and a computer-readable medium, embodiments thereof being defined by the dependent claims.

A first aspect of the invention is a method of operating a medical device. The medical device is configured to perform a medical procedure and comprises a set of processors and a set of memory units storing a software system for execution by the set of processors. The software system defines a plurality of subsystems, including a primary subsystem and a set of secondary subsystems. Each subsystem comprises software applications which are involved in the operation of the medical device during the medical procedure. The method comprises, during startup of the medical device: initiating each of the software applications; providing, by each of the software applications in the respective secondary subsystem when ready for startup, an application ready notification; providing, by the respective secondary subsystem when all of its software applications have provided the application ready notification, a subsystem ready notification; and coordinating, by the primary subsystem upon receiving the subsystem ready notification, startup of the set of secondary subsystems.

A second aspect of the invention is a medical device for performing a medical procedure. The medical device comprises a set of processors, and a set of memory units storing a software system for execution by the set of processors. The software system, when executed by the set of processors, operates the medical device to perform the medical procedure. The software system defines a plurality of subsystems, including a primary subsystem and a set of secondary subsystems. Each subsystem comprises software applications which are involved in the operation of the medical device during the medical procedure. The software system, when executed by the set of processors, performs a method in accordance with the first aspect or any of its embodiments.

A third aspect is a computer-readable medium comprising a software system for operating a medical device to perform a medical procedure. The software system defines a plurality of subsystems, including a primary subsystem and a set of secondary subsystems. Each subsystem comprises software applications which are involved in the operation of the medical device during the medical procedure. The software system, when executed by a set of processors of the medical device, performs the method in accordance with the first aspect or any of its embodiments.

These aspects enable deterministic startup of all relevant software applications of the software system in the medical device. The deterministic startup is enabled by separating the startup procedure into a preparation for startup on a subsystem level, by use of the application ready and subsystem ready notifications, and a preparation for startup on a system level, in which the primary subsystem coordinates startup of the individual subsystems. Further, the foregoing aspects enable the responsibility of ensuring that software applications are ready for startup to be delegated to the respective subsystem. Thereby, the startup procedure may be modularized in correspondence with the software system, so that each subsystem is operable to prepare for startup independent of other subsystems. Such a modularization is advantageous in that it allows the startup procedure to be separately implemented on the subsystems, the startup of which may be separately tested during development and deployment.

Further, the use of notifications enables safe and reliable startup of the medical device. For example, the software system may be prevented from being started when a malfunction occurs that prevents a notification from being provided. The use of notifications also enables simple and efficient detection and localization of malfunctions in the software system during startup of the medical device. Further, compared to the use of timers and nominal startup times as discussed in above, the use of the notifications may also shorten the time required for startup of the medical device.

A corresponding modularization may be implemented in a shutdown procedure, by the use of notifications, to prepare all relevant executing software applications in the medical device for a power loss in a deterministic, safe and reliable way.

Some embodiments of the first aspect are defined below and may serve the purpose of enabling, achieving or improving the deterministic startup and/or shutdown of all relevant processes of the software system for operating the medical device, or another purpose as understood by the skilled person.

In one embodiment, the method further comprises, in the respective subsystem: enabling, by the software applications of the respective secondary subsystem upon obtaining the subsystem ready notification, communication between the software applications of the respective secondary subsystem.

In one embodiment, the coordinating comprises: generating, by the primary subsystem, a system ready notification for receipt by the set of secondary subsystems.

In one embodiment, the coordinating further comprises: enabling, by the respective secondary subsystem upon obtaining the system ready notification, communication between at least a subset of the software applications of different subsystems among the plurality of subsystems, whereupon the medical device is ready to perform at least part of the medical procedure.

In one embodiment, the method further comprises: providing, by a respective software application in the primary subsystem when ready for startup, the application ready notification, wherein the coordinating is performed by the primary subsystem upon receiving the subsystem ready notification from the respective secondary subsystem and the application ready notification from the respective software application in the primary subsystem.

In one embodiment, a manager in the primary subsystem receives the subsystem ready notification from the respective secondary subsystem and the application ready notification from the respective software application in the primary subsystem and performs the coordinating.

In one embodiment, the respective secondary subsystem further comprises a manager, wherein the manager of the respective secondary subsystem provides the subsystem ready notification upon obtaining the application ready notification from all of its software applications.

In one embodiment, the coordinating comprises: providing, by a manager of the primary subsystem upon obtaining the application ready notification from each of the software applications of the primary subsystem and the subsystem ready notification from the respective secondary subsystem, a system ready notification for the respective secondary subsystem.

In one embodiment, the method further comprises: enabling, by the manager of the respective secondary subsystem upon obtaining the system ready notification and by the manager of the primary subsystem, communication between at least a subset of the software applications of different subsystems among the plurality of subsystems, whereupon the medical device is ready to perform at least part of the medical procedure.

In one embodiment, the software system defines at least two secondary subsystems, and the enabling communication between at least a subset of the software applications of different subsystems comprises: enabling direct communication between at least a subset of the software applications in the at least two secondary subsystems.

In one embodiment, the subsystems are executed on separate processors in the set of processors.

In one embodiment, two or more subsystems are critical to the medical procedure performed by the medical device and comprise a respective manager, and the method further comprises, during said startup: operating each of the managers of said two or more subsystems to send external heartbeat signals; and starting to monitor, mutually among the managers of said two or more subsystems, the external heartbeat signals for detection of an operational failure.

In one embodiment, the method further comprises, during said startup: reporting a first error, by the manager in the primary subsystem, when the application ready notification is not received from the respective software application of the primary subsystem within a first predefined time period; and reporting a second error, by the manager in the primary subsystem, when the subsystem ready notification is not received from the respective secondary subsystem within a second predefined time period.

In one embodiment, the method comprises, during shutdown of the medical device: providing, by a manager of the primary subsystem, a shutdown notification for the set of secondary subsystems; requesting, by the manager of the primary subsystem, termination of the software applications of the primary subsystem; and requesting, by a manager of the respective secondary subsystem after obtaining the shutdown notification, termination of the software applications of the respective secondary subsystem.

In one embodiment, the requesting termination of the software applications of the respective secondary subsystem comprises, for at least one secondary subsystem: providing, by the manager, a subsystem not ready notification for the software applications of the secondary subsystem; preparing for termination, by at least a subset of the software applications of the secondary subsystem upon obtaining the subsystem not ready notification; providing, by said at least a subset of the software applications when prepared for termination, an application ready for shutdown notification; and providing, by the manager of the secondary subsystem upon obtaining the application ready for shutdown notification from said at least a subset of the software applications, a subsystem ready for shutdown notification for the manager of the primary subsystem.

In one embodiment, the requesting termination of the software applications of the primary subsystem comprises: providing, by the manager of the primary subsystem, a subsystem not ready notification for the software applications of the primary subsystem; preparing for termination, by at least a subset of the software applications of the primary subsystem upon obtaining the subsystem not ready notification; and providing, by said at least a subset of the software applications of the primary subsystem when prepared for termination, an application ready for shutdown notification.

In one embodiment, the method further comprises: initiating power loss of the medical device, by the manager of the primary subsystem upon obtaining the subsystem ready for shutdown notification from said at least one secondary subsystem and the application ready for shutdown notification from said at least a subset of the software applications of the primary subsystem.

In one embodiment, the method comprises: setting, in absence of errors during said shutdown and by at least one of the managers, a shutdown reason parameter to indicate normal shutdown and storing the shutdown reason parameter in the set of memory units; and setting, during said startup and by said at least one of the managers, the shutdown reason parameter to indicate a shutdown error and storing the shutdown reason parameter in the set of memory units.

In one embodiment, the software applications comprises one or more critical software applications, which are critical to the medical procedure performed by the medical device, and the method further comprises, during shutdown of the medical device and before providing the shutdown notification for the set of secondary subsystems: providing, by the manager of the primary subsystem, a shutdown request for the one or more critical software applications; validating, by the one or more critical software applications, the shutdown request in view of the operation of the medical device; and providing, by at least one of the one or more critical software applications and if shutdown is acceptable, an application ready for shutdown notification; wherein the manager of the primary subsystem, upon obtaining the application ready for shutdown notification from said at least one of the one or more critical software applications, provides the shutdown notification for the set of secondary subsystems.

In one embodiment, the plurality of subsystems comprises a first subsystem with a software application for controlling the medical device to perform the medical procedure, and a second subsystem with a software application for communicating with an actuator and/or a sensor of the medical device, and the coordinating enables communication between the software application for controlling the medical device and the software application for communicating.

In one embodiment, the plurality of subsystems further comprises a third subsystem with a software application for supervising the medical procedure for detection of deviations, and fourth subsystem with a software application for communicating with an auxiliary sensor of the medical device, and the coordinating further enables communication between the software application for supervising the medical procedure and the software application for communicating with the auxiliary sensor, and between the software application for controlling the medical device and the software application for supervising the medical procedure.

A further aspect of the invention is a method of operating a medical device. The medical device is configured to perform a medical procedure and comprises a set of processors and a set of memory units storing a software system for execution by the set of processors. The software system defines a plurality of subsystems, including a primary subsystem and a set of secondary subsystems. Each subsystem comprises software applications which are involved in the operation of the medical device during the medical procedure. The method comprises, during startup of the medical device: initiating each of the software applications; providing, by each of the software applications when ready for startup, an application ready notification; providing, by the respective subsystem when all of its software applications have provided the application ready notification, a subsystem ready notification; and coordinating, by the primary subsystem upon receiving the subsystem ready notification, startup of the subsystems. The method may be deployed on a medical device corresponding to the second aspect and implemented on a computer-readable medium corresponding to the third aspect. The foregoing embodiments are equally applicable to the method of the further aspect.

Still other objectives and aspects, as well as embodiments, features, technical effects and advantages of the present invention may appear from the following detailed description, from the attached claims as well as from the drawings.

BRIEF DESCRIPTION OF THE DRAWINGS

Embodiments of the invention will now be described in more detail with reference to the accompanying drawings.

FIGS. 5A-5D are flow charts of methods performed for shutdown of a medical device in accordance with embodiments of the invention.

DETAILED DESCRIPTION OF EXAMPLE EMBODIMENTS

Figure 1A:
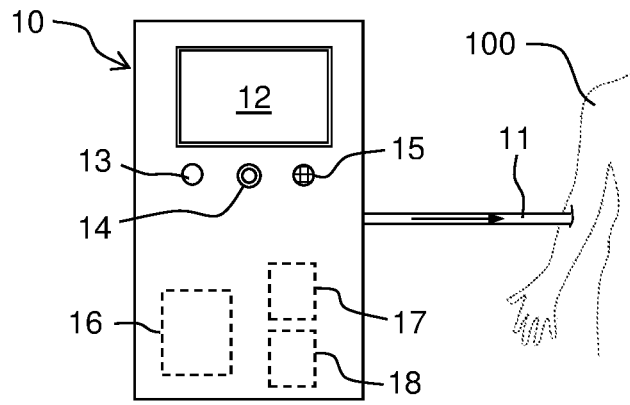
FIGS. 1A-1C show examples of medical devices that may implement embodiments of the invention.

Embodiments of the present invention will now be described more fully hereinafter with reference to the accompanying drawings, in which some, but not all, embodiments of the invention are shown. Indeed, the inventive solution may be embodied in many different forms and should not be construed as limited to the embodiments set forth herein; rather, these embodiments are provided so that this disclosure may satisfy applicable legal requirements. Like numbers refer to like elements throughout.

Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more," even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention. As used herein, a "set" of items is intended to imply a provision of one or more items.

It will furthermore be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing the scope of the present invention. As used herein, the term "and/or" includes any and all combinations of one or more of the associated listed items.

Well-known functions or constructions may not be described in detail for brevity and/or clarity. Unless otherwise defined, all terms (including technical and scientific terms) used herein have the same meaning as commonly understood by one of ordinary skill in the art to which this invention belongs.

Embodiments of the invention are directed to techniques that enable deterministic startup and/or shutdown of all relevant processes of a medical software system for operating a medical device. The medical device is an automated apparatus or machine which is configured to be operated, optionally in combination with one or more other medical devices, to perform a medical procedure in relation to a human or animal subject. As used herein, a medical procedure may involve one or more of diagnosis, prevention, monitoring, treatment or alleviation of a disease, an injury, or a handicap, or monitoring for detection thereof. In the following, it is presumed that the medical software system comprises two or more subsystems, which are executed on one or more processors to control the medical device to perform the medical procedure. The subsystems may be seen as software modules of computer-executable instructions that may be independently developed and tested to provide specific functionality in relation to the operation of medical device when performing the medical procedure. The respective subsystem comprises a set of software applications, where each software application corresponds to a process or task executed within the context of the respective subsystem. The software applications within a subsystem may thus be designed to perform a group of coordinated processes to provide the specific functionality of the subsystem. However, it is conceivable that a subsystem includes one or more software applications that are not involved in the operation of the medical device. Further, the subsystem may include further software components, such as middleware and/or low-level software components that perform basic functions or services in the software system, such as a communication stack for managing communication with other subsystems, an error manager for managing technical errors, a notification manager for managing notifications, etc. One or more of the subsystems may be operated on top of one or more operating systems to make use of services provided by the operating system(s) in relation to hardware and software resources. Depending on implementation, the operating system(s) may, e.g., include a real-time operating system, an embedded operating system, a single-tasking operating system, or a multi-tasking operating system, or any combination thereof. It is also conceivable that one or more of the subsystems is configured to operate without an operating system and directly interface the hardware resources of the medical device.

Figure 1B:
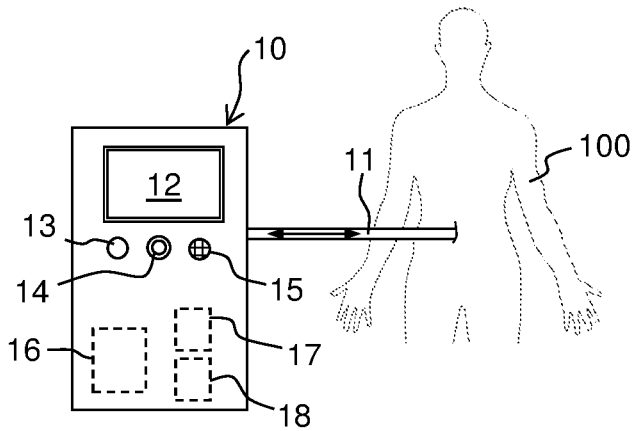
Figure 1C:
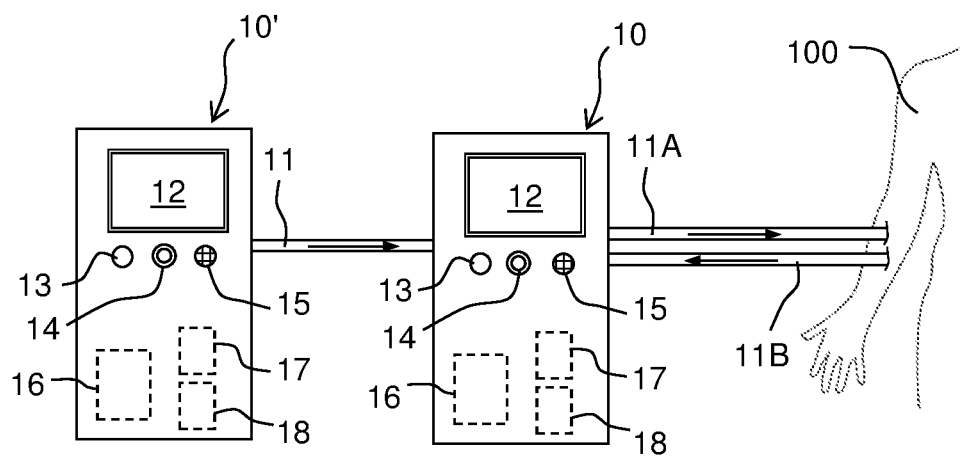

FIGS. 1A-1C are schematic views of examples medical devices that are directly or indirectly connected in fluid communication with the subject. It should be noted that the illustrated examples are highly schematic and are given for the sole purpose of illustrating different implementation contexts for embodiments of the present invention.

FIG. 1A illustrates a medical device 10 which is operable to deliver a medical fluid into the body of a subject 100 in a controlled manner, as indicated by an arrow, e.g. into the circulatory system of the subject 100. The medical fluid may be any suitable liquid, including but not limited to medication and/or nutrients. This type of medical device 10 is commonly known as an "infusion pump". In the illustrated simplified example, the medical device 10 comprises a fluid line 11 for connection to the subject 100, a display 12, control buttons 13 (one shown), an indicator lamp 14, a loudspeaker 15, a control system 16, one or more actuators 17 for controlled delivery of the medical fluid to the subject 100 via the fluid line 11, and one or more sensors 18 for providing sensor data indicative of the infusion process performed by the infusion pump. The actuator(s) 17 and sensor(s) 18 may include internal components (as indicated by dashed lines) or external components of the medical device 10, or both. The control system 16 is configured to coordinate the operation of the actuator(s) 17 and the sensor(s) 18 to perform the intended medical procedure of the infusion pump, as well as operate the display 12, the indicator lamp, 14 and the loudspeaker 15 as needed in connection with the medical procedure, and obtain user input via the control buttons 13. For example, the display 12 may be operated to present instructions to the user of the medical device 10, the indicator lamp 14 may be operated to indicate a device status, and loudspeaker 15 may be operated to generate an alarm signal, etc.

FIG. 1B illustrates a medical device 10 which is operable to, in a controlled manner, deliver a dialysis fluid to the abdominal cavity of a subject 100 and subsequently remove the dialysis fluid therefrom, as indicated by a double-ended arrow. This medical procedure is commonly known as automated peritoneal dialysis, and the medical device 10 is often denoted a "PD cycler". The medical device 10 in FIG. 1B may have a similar set of components as the medical device 10 in FIG. 1A, on the illustrated level of detail, and will not be described further.

FIG. 1C illustrates two medical devices 10, 10' which may be involved in a medical procedure of performing extracorporeal blood treatment, e.g. as part of renal replacement therapy, such as hemodialysis, hemodiafiltration, hemofiltration or ultrafiltration. The medical device denoted 10 is a blood treatment apparatus, which comprises a blood withdrawal line 11A and a blood return line 11B for connection to the circulatory system of a subject 100, e.g. at a blood vessel access. As indicated by arrows, the medical device 10 is operable to withdraw blood from the subject 100, process the blood and return the processed blood to the subject 100 in a controlled manner. The medical device denoted 10' is operable to prepare a fluid for use by the blood treatment apparatus 10 and comprises a fluid line 11 for supplying the fluid to the blood treatment apparatus 10. In one example, the medical device 10' is a water preparation apparatus and the fluid is purified water. For example, the water treatment apparatus 10' may filter incoming water by reverse osmosis as known in the art. Each of the medical devices 10, 10' in FIG. 1C may have a similar set of components as the medical device 10 in FIG. 1A, on the illustrated level of detail, and will not be described further.

Figure 2:
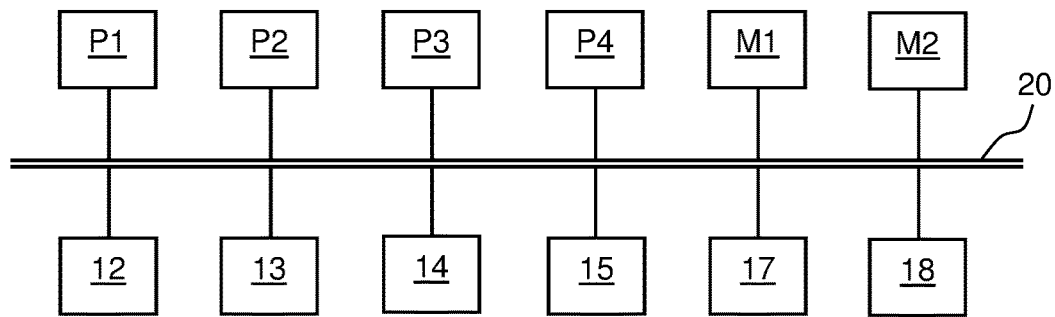
FIG. 2 is a schematic block diagram of hardware components of a medical device connected to a signal communication structure.

FIG. 2 shows an example of hardware components that may be active during the operation of the medical device, e.g. as depicted in FIGS. 1A-1C, and the interconnection of such hardware components. In the illustrated example, the hardware components are connected for signal exchange over a signal communication structure 20, which may include any form of bus structure or switch fabric structure and/or individual wirings. It is also conceivable that one or more of the components are located on a common substrate, e.g. in an integrated circuit (IC) or the like, and are interconnected by signal conducting tracks on the common substrate, which in turn is connected to other components by the signal communication structure 20. In the example of FIG. 2, the medical device comprises four separate processors P1-P4, two separate memory units M1-M2, in addition to display 12, control button 13, indicator lamp 14, loudspeaker 15, actuator 17 and sensor 18. The processors P1-P4 and memory units M1-M2 are "separate" in the sense that they are individually operable units, while they may or may not be located in any combination on a common substrate, e.g. in an IC. The respective processor P1-P4 may be any commercially available processing device, such as a CPU, DSP, a microprocessor, an FPGA, an ASIC, or any other electronic programmable logic device, or a combination thereof. The respective memory unit M1-M2 may include non-volatile memory or volatile memory, or a combination thereof, including but not limited to ROM, PROM, EEPROM, flash memory, removable memory, RAM, DRAM, SRAM, cache memory, hard drive, storage medium, etc.

In the example of FIG. 2, the above-mentioned software system may be stored on one or more of the memory units M1-M2, for execution by one or more of the processors P1-P4. The control system 16 in FIGS. 1A-1C may thereby be implemented by the software system when executed by one or more of the processors P1-P4.

The software system may be provided for installation on the medical device on any suitable computer-readable medium (CRM). The CRM may comprise a non-transitory storage or memory medium, whether volatile or non-volatile, such as an electronic, magnetic or optical medium. Alternatively or additionally, the CRM may comprise a transitory medium such as a propagating signal, whether electric, electromagnetic or digital, which may be conveyed via a communication medium such as a network and/or a wireless link.

The hardware components in FIG. 2 are merely given as an example. The medical device 10, 10' may include any number of each type of component, and some of the components in FIG. 2 may be omitted or replaced depending on the desired functionality of the medical device. For example, if the display 12 is touch-sensitive, control buttons 13 may be replaced by virtual buttons on the display 12. It is also realized that the example in FIG. 2 is non-exhaustive and that the medical device may include other types of components that are active during its operation, such a keyboard, a computer mouse, a power supply, etc.

Generally, the medical device 10, 10' comprises at least one processor, at least one memory unit and at least one of an actuator and a sensor. The medical devices 10, 10' in FIGS. 1A-1C generally comprise at least one actuator 17, and may also comprise at least one sensor 18. A medical device which is designed for monitoring may principally include at least one sensor 18, but need not include an actuator 17. In the examples of FIGS. 1A-1C, the actuator(s) 17 may include one or more of a fluid pump, a valve, a heater, a cleaning system, etc, and the sensor(s) 18 may be configured to generate sensor data representative of one or more of temperature, conductivity, concentration, pressure, flow rate, etc.

Figure 3:
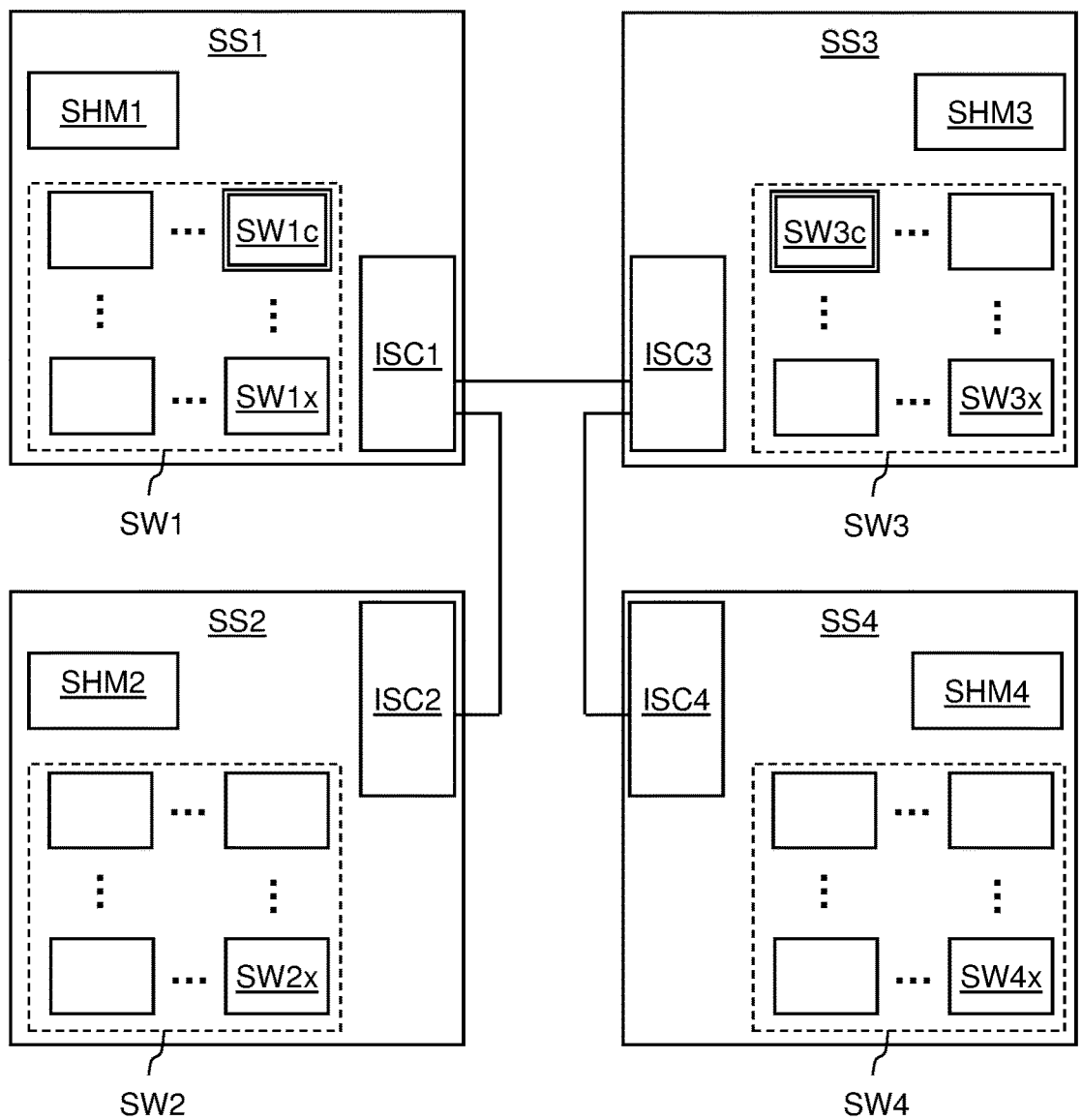
FIG. 3 is a schematic block diagram of a software system for operating a medical device.

FIG. 3 is a block diagram of a software system for execution in a medical device, e.g. any of the medical devices previously described, in accordance with a non-limiting example. As shown, the software system comprises four subsystems SS1-SS4. In the following, it is assumed that the subsystems SS1-SS4 are executed on one or more separate processors. In the example of FIG. 2, subsystems SS1-SS4 may be executed on a respective processor P1-P4. In other words, in some embodiments, the subsystem SS1 may be executed on the processor P1, the subsystem SS2 may be executed on the processor P2, the subsystem SS3 may be executed on the processor P3 and/or the subsystem SS4 may be executed on the processor P4. Each subsystem SS1-SS4 comprises a set of software applications that are involved in the operation of the medical device while it performs the medical procedure. The set of software applications in subsystem SS1, SS2, SS3, SS4 is collectively designated by SW1, SW2, SW3, SW4, respectively. An individual software application in subsystem SS1, SS2, SS3, SS4 is designated by software applications SW1$x$, SW2$x$, SW3$x$, SW4$x$, respectively. Further, each subsystem SS1-SS4 includes a respective communication module, denoted ISC1-ISC4, which includes the above-mentioned communication stack and is responsible for managing communication with one or more of the other subsystems. In the illustrated example, ISC1-ISC4 are configured to establish communication between subsystems SS1 and SS3, between subsystems SS1 and SS2, and between subsystems SS3 and SS4. In accordance with an embodiment, each subsystem SS1-SS4 further comprises a manager module, designated by SHM1-SHM4 and denoted "manager" in the following. The respective manager SHM1-SHM4 is responsible for managing the operation of its subsystem SS1-SS4 during startup and shutdown. The respective manager SHM1-SHM4 has access to a list of the software applications to be managed. The managers SHM1-SHM4 may also be responsible for monitoring the health of the software system during operation, e.g. by the respective manager SHM1-SHM4 monitoring that its software applications SW1-SW4 are running as expected. One or more of the managers SHM1-SHM4 may also contain boot code, which is executed at startup to prepare the system for loading and running an operating system on one or more of the processors P1-P4.

In the example of FIG. 3, subsystem SS1 comprises a software application designated by SW1$c$, and subsystem SS3 comprises a software application designated by SW3$c$. The software applications SW1$c$ and SW3$c$ are distinguished from the other software applications by being critical to the operation of the medical device when performing the medical procedure. In this context, "critical" implies that correct operation of the respective software application SW1$c$, SW3$c$ is necessary for the medical procedure to be performed in accordance with a requirement specification, which may be set by the manufacturer and/or by regulatory authorities, e.g. in view of mitigating health risks for the subject 100. A subsystem that includes at least one critical software application is also denoted "critical subsystem" herein. In one example, a critical software application may be configured to control the medical procedure that is performed by the medical device, e.g. by generating an ordered sequence of control commands or signals for operating one or more actuators 17 and, optionally, one or more sensors 18. In another example, a critical software application may be configured to supervise the operation of the medical procedure that is performed by the medical device, e.g. by generating an ordered sequence of control commands or signals for operating one or more sensors 18.

In one specific example, SW1$c$ is configured to control the medical procedure and SW3$c$ is configured to supervise the operation of the medical procedure. Many medical devices that perform a medical procedure that poses a health risk to the subject in case of operational failure in the main system that controls the medical procedure, or any of the hardware components used by such a main system, are required to include a protective system that operates in parallel and is independent of the main system. Whenever the protective system detects a potential operational failure, the medical device is switched to a safe operating condition. Thus, reverting to FIG. 3, subsystem SS1 may correspond to the main system, and subsystem SS3 may correspond to the protective system. The subsystems SS2 and SS4 may be configured to communicate with different sets of actuators and/or sensors based on commands/signals generated by subsystem SS1 and subsystem SS3, respectively. To this end, each of the subsystems SS2, SS4 may comprise a software application for providing access to peripherals (e.g. actuators and/or sensors) connected to the respective subsystem SS2, SS4. To achieve the independence between the main system and the protective system, SS2 may be connected to a set of main sensors and SS4 may be connected to a separate set of auxiliary sensors. The subsystems SS1-SS4 may also be implemented on separate processors (e.g. P1-P4 in FIG. 2) to achieve independence. In a variant, subsystem SS2 and/or subsystem SS4 may be included within subsystem SS1 and subsystem SS3, respectively.

Thus, in one implementation, the software system may comprise at least a main system (subsystem SS1) and a protective system (subsystem SS3), which may be a monitoring and fail-safe component, fully redundant to subsystem SS1 to help ensure safety of a patient at all times. Subsystem SS3 may be designed such that any single point of failure of subsystem SS1 that poses a hazard to the patient may be detected and averted by subsystem SS3. Under normal conditions, subsystem SS1 will read the current state of HW and/or SW components, determine the next state according to the selected mode of operation, and write new states to the HW and/or SW components as necessary. Because of the risk of error inherent to each of these three phases of operation, subsystem SS3 is implemented to protect the patient in the event of a failure, by halting the system and notifying the operator of the failure condition. Possible failures may include a loss or misrepresentation of data, a miscalculation or fault in the software, or a hardware failure, for example, of a transducer, switch or processor. Subsystem SS3 protects against such risks by monitoring commands and status information sent in the system. Subsystem SS3 may also be connected to one or more dedicated sensors to provide redundant measurements. It may be noted that the link between subsystems need not be a single connection but may comprise a series of links such as one or more of integrated circuits, digital logic, I/O buses and software.

Below follows an example of software applications that may be included in subsystem SS3. It should be understood that this is merely an example given to increase understanding and provide additional context. Subsystem SS3 may thus contain further, fewer or other software applications. It should also be clear that the following example structure, or part thereof, may also be implemented within other subsystems of the system, e.g. in subsystem SS1. In one specific example, subsystem SS3 comprises an I/O application ("I/O"), which is responsible for implementing low level SW to HW, except for serial communication. Thus, the I/O provides I/O data to clients and may also perform CRC of the I/O data. An Alarm Handling application is responsible for managing alarms and requesting reset through the I/O when an alarm is active. During operation of the medical device, the Alarm Handling application interacts with the Mode Management application (below) and the I/O. A Configuration Handling application is responsible for providing the therapy settings to clients within subsystem SS3. During operation of the medical device, the Configuration Handling application interacts with subsystem SS1 via Inter System Handling (below). A Data Logger application is responsible for receiving text-based log data from other software applications within subsystem SS3 and provides the log data to clients. During operation of the medical device, the Data Logger application also interacts with the Time Handling application (below). A Mode Management application is responsible for providing current system state and therapy state to clients. The states are received from subsystem SS1, via Inter System Handling (below) and the I/O. A Time Handling application provides the current system time to clients. A Device Supervision application is responsible for monitoring ongoing therapy, using values retrieved from the I/O. If subsystem SS1 does not take preventive action in time, the Device Supervision application is responsible for reporting an alarm to the Alarm Handling application. During operation of the medical device, the Device Supervision application also interacts with the Configuration Handling application, the Mode Management application, the Time Handling application, and the Software Health Monitoring software module (below). The Device Supervision application may monitor states and state changes in subsystem SS1. In the context of a medical device, for example as exemplified with reference to FIGS. 1A-1C, the Device Supervision application may also monitor the operation (values, commands, status, timing, etc.) of one or more blood leak detectors, one or more weight scales, one or more clamps, one or more air bubble detectors, one or more pumps (syringe pump, blood pump, dialysis fluid pump, effluent pump, replacement pump, etc.), one or more pinch valves, one or more control panels, one or more liquid leak detectors, one or more pressure sensors, etc. Subsystem SS3 further comprises a Software Health Monitoring software module, corresponding to SHM3 in FIG. 3, which is responsible for monitoring the health of the software in subsystem SS3 and to monitor that subsystem SS1 is alive and running. Examples include checking integrity of the software, checking RAM, monitoring that all software applications within subsystem SS3 are running as expected, monitor subsystem SS1 to verify that it is up and running, and kicking the hardware (HW) watchdog. Subsystem SS3 also comprises an Inter System Communication software module, corresponding to ISC3 in FIG. 3, which is responsible for managing serial communication with other subsystems, including subsystem SS1. Inter System Communication may be sub-divided into Inter System Handling for high level communication, and Inter System Transport for low level communication. In one implementation example, Alarm Handling, Configuration Handling, Data Logger, Mode Management and Time Handling are thread safe libraries which execute in the context of the client, and Software Health Monitoring is executed as a task and is event driven to act on incoming events. The Software Health Monitoring task also has a cyclic event of a predefined time period, e.g. 50 ms, to handle timeouts. The Software Health Monitoring task has highest priority to avoid that other tasks block the task supervision. Device Supervision is executed as a task and has cycle execution, e.g. of 50 ms, and high priority to execute on the required timing. The I/O is executed as a task and is event driven to service the I/O events and has cyclic execution, e.g. of 5 ms, for independent signal reading and bus buffer emptying. The I/O task has medium priority to be able to service events in a short time frame while at the same time avoiding blocking the Device Supervision tasks. The Inter System Communication is executed as a task and is event driven, since the responsibilities of Inter System Communication are to handle ingoing and outgoing communication events. The Inter System Communication task also has a cycle execution, e.g. of 100 ms, for supervision of system state messages. The Inter System Communication task has low priority, since the real-time requirements of this task are the lowest. Communication between the tasks is non-blocking; a higher prioritized task may not be blocked by communicating with a lower prioritized task.

Figure 4A:
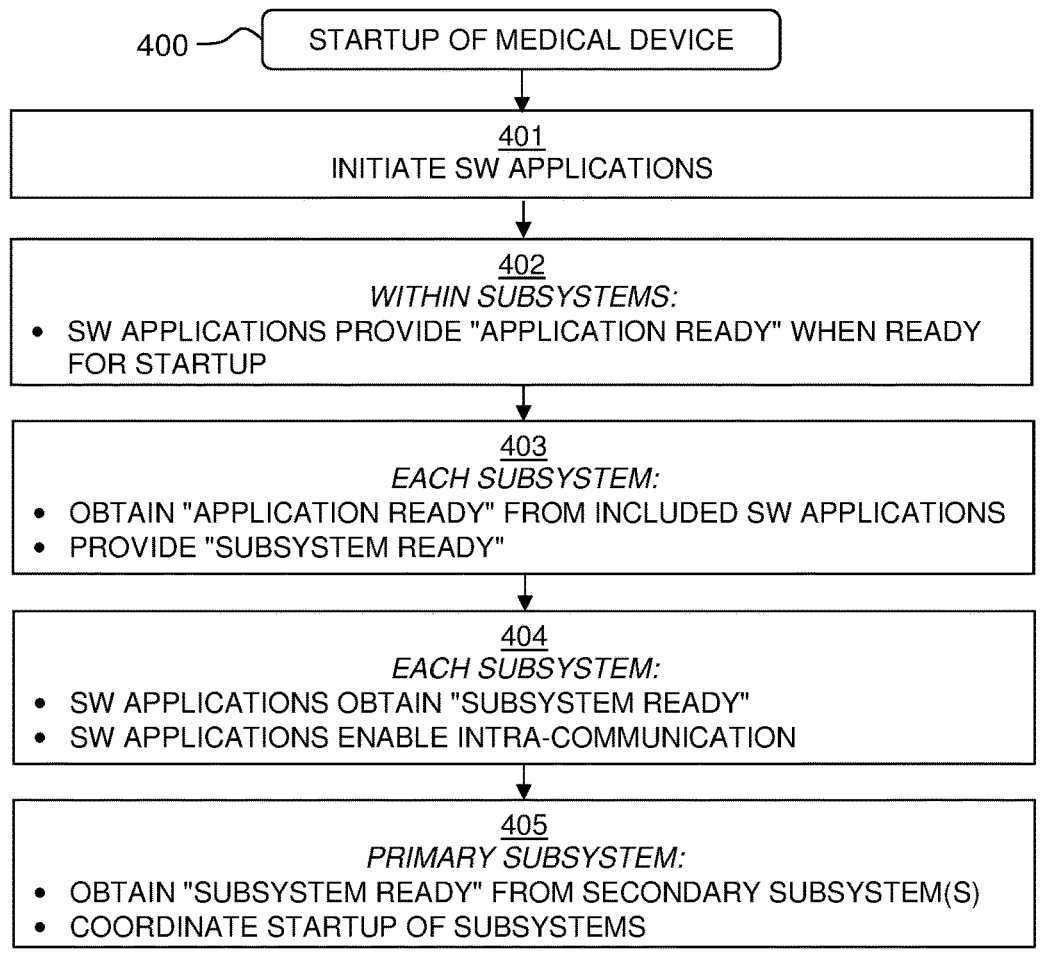
FIGS. 4A-4B are flow charts of methods performed for startup of a medical device in accordance with embodiments of the invention.

FIG. 4A is a flow chart of an embodiment of a method 400 for startup of a medical device that comprises the software system in FIG. 3. The method 400 presumes that one of the subsystems is a "primary subsystem", which coordinates the startup of the subsystems, whereas the remaining subsystems are denoted "secondary subsystems". The method is generally applicable to any software system that comprises one primary subsystem and at least one secondary subsystem. In the following example, SS1 is the primary subsystem, and SS2-SS4 are secondary subsystems. In the following example, it is also presumed that the managers SHM1-SHM4 are controllers for the startup of the system, as described in the following.

The method 400 comprises a step 401 of initiating the individual software applications SW1x-SW4x in all of the subsystems SS1-SS4. Step 401 may be performed subsequent to or as part of a conventional boot procedure, which initiates system functions and system communication within the software system, including starting the managers SHM1-SHM4 and the communication modules ISC1-ISC4 of the subsystems SS1-SS4. Step 401 may be performed automatically upon power up of the medical device. In one embodiment of step 401, the software applications SW1-SW4 in the respective subsystem initiate upon receipt of a start command/signal which may be generated by the manager SHM1-SHM4 of the respective subsystem SS1-SS4 or elsewhere in the software system. During the initiation in step 401, the respective software application SW1-SW4 may complete a respective predefined sequence of initiation actions, such as reading from a memory (cf. memory units M1, M2 in FIG. 2), initiating one or more parameters, starting a communication interface, etc. It may be noted that the present disclosure presumes that all of the software applications SW1-SW4, shown in FIG. 3, are to be started by the startup method 400. However, it is conceivable that one or more of the subsystems SS1-SS4 includes one or more software applications which are involved in the operation of the medical device for performing the medical procedure but which are started at another time, i.e. separate from the startup method 400.

In step 402, when the respective software application SW1x-SW4x has been initiated according to step 401, the software application provides an "application ready" notification within its respective subsystem SS1-SS4 indicating that the software application is ready for startup. In this context, a software application is "ready for startup" when it is ready to perform its designated task or process and to interact with other software applications. In one embodiment, the "application ready" notification is provided by a software application whenever it is operative to the extent that it is prepared to receive incoming communication signals from other software applications. In some embodiments, the software application is also prepared to send communication signals to other software applications, e.g. by a request-response message exchange pattern. Thus, the software applications need not be fully operative when providing the "application ready" notification.

Step 403 is performed by each subsystem SS1-SS4 separately. When the manager SHM1-SHM4 of the respective subsystem SS1-SS4 has obtained the "application ready" notification from all of the software applications SW1-SW4 in the respective subsystem SS1-SS4, the manager SHM1-SHM4 provides a "subsystem ready" notification within the software system, both internally within the respective subsystem SS1-SS4 and externally for receipt by the primary subsystem SS1 (in step 405 below).

Step 404 is also performed by each subsystem SS1-SS4 separately. When each of the software applications SW1-SW4 in the subsystem SS1-SS4 has obtained the "subsystem ready" notification provided by the manager SHM1-SHM4 of the subsystem SS1-SS4, the software applications SW1-SW4 enable communication between themselves, i.e. within the respective subsystem SS1-SS4. Hence, step 404 allows application-level "intra-communication" within the respective subsystem SS1-SS4. When step 404 is completed, all of the software applications in the subsystem have been started and the subsystem is thereby ready to interact with other subsystems in the software system.

Step 405 is performed by the primary subsystem SS1 only. When the manager SHM1 has obtained the "subsystem ready" notification of all secondary subsystems, the manager SHM1 coordinates startup of the subsystems SS1-SS4.

The method 400 enables a deterministic startup of the software system of the medical device, by separating the startup into a subsystem level and a system level, and by first ensuring that all software applications are ready for startup on a subsystem level and then ensuring that all subsystems are ready for startup on a system level before proceeding to startup. This principle is further illustrated in FIG. 6, which illustrates the states of the software system on a subsystem level (top) and a system level (bottom) during startup and shutdown. It is important to note that FIG. 6 does not imply that the software system is necessarily implemented as a state machine, but is merely intended to explain the overall control mechanisms during startup and shutdown of the software system. When the medical device is switched on and powered up (transitions Ia and Ib in FIG. 6), the software system is in state "system not ready", and each of the subsystems SS1-SS4 is in state "subsystem not ready". As a result of steps 401-404, corresponding to transition II in FIG. 6, the respective subsystem SS1-SS4 enters state "subsystem ready" (after receiving the "application ready" notification from its software applications). On a system level, the software system is still in state "system not ready". As a result of step 405, corresponding to transition III in FIG. 6, the software system enters state "system ready" (after receiving the "subsystem ready" notifications from the secondary subsystems) and the software system is now ready to proceed to operate the medical device for performing the medical procedure. It should be understood that the use of the "application ready" notification and the "subsystem ready" notification ensures a safe and reliable startup of the medical device. For example, the notifications prevent the software system from being started whenever a malfunction occurs that prevents a notification from being provided. The use of notifications enables simple and efficient detection and localization of malfunctions in the software system. Further, compared to the use of timers and nominal startup times as discussed in the Background section, the use of the notifications may also shorten the time required for startup of the medical device, since the nominal startup times are generally set with a significant margin to the actual startup times.

It is also worth noting that a common "subsystem ready" notification is received in step 404 by all software applications within a subsystem and triggers the individual software applications to enable the application-level intra-communication within this subsystem. By steps 401-404, the startup method 400 provides a distributed yet deterministic startup of the respective subsystem. This means in turn that the method 400 dispenses with any need for centralized control of the start order of individual software applications within the respective subsystem, and instead all of these software applications are allowed to start whenever they receive the "subsystem ready" notification. The skilled person realizes that this distributed startup of software applications not only facilitates control and troubleshooting of the startup procedure, but also facilitates maintenance and updating of the software system by facilitating addition and removal of software applications.

The notifications may be distributed in the software system by a push mechanism or a pull mechanism as is well-known in the art. With a push mechanism, the notification, or a message indicating that a notification is available, is sent from the originator for receipt or interception by the recipient. With a poll mechanism, the recipient requests the notification from the originator.

Reverting to FIG. 4A, it may be noted that the "application ready" notification need not be provided, within the respective subsystem SS1-SS4, from the respective software application directly to the manager SHM1-SHM4. Instead, the software applications within a subsystem may provide their "application ready" notifications in a predefined sequence from one software application to the next. When the final software application in the sequence then provides its "application ready" notification to the manager, the manager concludes that all "application ready" notifications have been provided in the subsystem.

It is also conceivable to replace the distributed managers SHM1-SHM4 in FIG. 3 by a central manager which obtains the "application ready" notifications and the "subsystem ready notifications" as described above. However, distributed managers SHM1-SHM4 offer the advantage of strict modularization of subsystems SS1-SS4, which in turn enables the subsystems SS1-SS4 to be independently developed and/or tested and/or deployed.

In a further variant, the functionality of the managers SHM1-SHM4 is instead performed by one of the software applications in the respective subsystem SS1-SS4.

It may also be noted that while step 404 in FIG. 4A provides the advantage of ensuring that, when the subsystem enters state "subsystem ready", the software applications within a subsystem are enabled to communicate with each other and the subsystem is truly ready for startup, it is conceivable that this intra-communication of the subsystems is enabled at a later stage, e.g. when the software system enters state "system ready" (e.g. in step 408 below).

In a still further variant, only the software applications in the secondary subsystems SS2-SS4 are configured to provide "application ready" notifications and receive "subsystem ready" notifications from their respective manager SHM2-SHM4, whereas software applications in the primary subsystem SS1 are not.

Figure 4B:
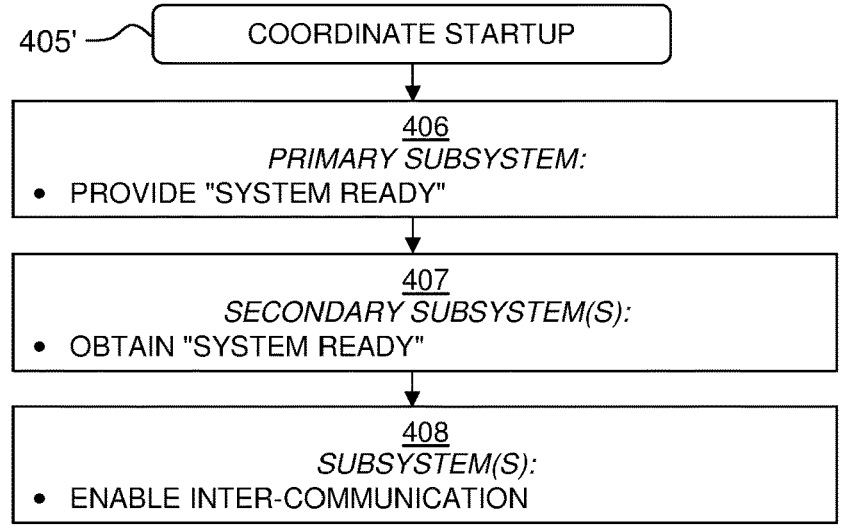

FIG. 4B is a flow chart of an embodiment of a method 405' for coordinating the startup of the subsystems SS1-SS4, which may be performed as part of step 405 in FIG. 4A. In step 406, the primary subsystem SS1 provides a "system ready" notification for the respective secondary subsystem SS2-SS4. Reverting to FIG. 4A, it should be understood that the "system ready" notification is generated when the primary subsystem SS1 both has obtained the "application ready" notification from all of its software applications SW1 (step 403) and the "subsystem ready" notification from all of the secondary subsystems SS2-SS4 (step 405). In step 407, the respective secondary subsystem SS2-SS4 obtains the "system ready" notification. By obtaining the "system ready" notification, the managers SHM2-SHM4 are made aware that all subsystems SS1-SS4 are ready for startup. Likewise, the manager SHM1 is aware that all subsystems are ready for startup. As understood from the foregoing, a subsystem is ready for startup when its software applications have been started and are allowed to communicate with each other.

In subsequent step 408, the managers SHM1-SHM4 of all subsystems SS1-SS4 enable application-level communication between the subsystems, so that a software application in one subsystem is able to communicate with a software application in another subsystem. Hence, step 408 enables "inter-communication" between subsystems SS1-SS4. In the example of FIG. 3, communication is enabled between SS1 and SS2, SS1 and SS3, and SS3 and SS4. Thus, step 408 may not only enable centralized communication, i.e. between the primary subsystem and one or more secondary subsystems, but also direct communication between secondary subsystems. When step 408 is completed, the software system has been started and the medical device is ready to perform at least part of the medical procedure, e.g. by providing instructions to an operator, allowing an operator to enter control parameter values for the medical procedure, etc.

The method 405' ensures a deterministic startup of all subsystems SS1-SS4. The advantages of providing the "system ready" notification are similar to the advantages of providing the "application ready" and "subsystem ready" notifications as explained above. For example, it may be noted that a common "system ready" notification is received in step 407 by all secondary subsystems within the software system and triggers the individual secondary subsystems to enable inter-subsystem communication within the software system. By steps 406-408, the startup method 400 provides a distributed yet deterministic startup of the software system. This means in turn that the method 400 dispenses with any need for centralized control of the start order of individual subsystems within the software system, and instead all of the subsystems are allowed to start whenever they receive the "system ready" notification. The skilled person realizes that this distributed startup of subsystems not only facilitates control and troubleshooting of the startup procedure, but also facilitates maintenance and updating of the software system by facilitating addition and removal of subsystems.

FIG. 5A is a flow chart of an embodiment of a method 500 for shutdown of a medical device operated by the software system in FIG. 3. The shutdown may be triggered by a shutdown command generated by an operator, e.g. when pressing a control button (cf. 13 in FIGS. 1A-1C), or by a process in the medical device.

In step 501, the manager SHM1 of the primary subsystem SS1 is notified about the shutdown command and proceeds to initiate shutdown by providing a "shutdown" notification for all secondary subsystems SS2-SS4. In step 502, the manager SHM1 requests termination of the software applications SW1 in the primary subsystem SS1. In this context, "terminate" implies that each software application stops its activities to the extent that it is prepared for a power loss. Step 503 is performed by each secondary subsystem SS2-SS4 separately. The manager SHM2-SHM4 obtains the "shutdown" notification and then requests termination of the software applications SW2-SW4 of the secondary subsystem SS2-SS4. Then, in step 504, the manager SHM1 of the primary subsystem SS1 initiates power loss of the medical device, e.g. by notifying a power manager in the medical device to cut the power.

The combination of steps 501-503 ensures a deterministic shutdown of the medical device, by separating the shutdown into a system level and a subsystem level. This principle is further illustrated in FIG. 6. When the medical device is to be shutdown, the software system is in state "system ready" and each of the subsystems SS1-SS4 is in state "subsystem ready". As a result of step 501, corresponding to transition IV in FIG. 6, the system may be seen to enter state "system not ready". On the subsystem level, the subsystems SS1-SS4 are still in state "subsystem ready" after step 501. As a result of steps 502-503, the respective subsystem SS1-SS4 may be seen to enter state "subsystem not ready, corresponding to transition V in FIG. 6. Thereby, the software system is prepared on both system level and subsystem level for a power loss, which is then initiated by step 504 and corresponds to transition VI in FIG. 6.

FIG. 5B is a flow chart of an embodiment of a method 502' for requesting termination of the software applications SW1 of the primary subsystem SS1, which may be performed as part of step 502 in FIG. 5A. In step 505, the manager SHM1 provides a "subsystem not ready" notification for the software applications SW1 of the primary subsystem SS1. In step 506, the software applications obtain the "subsystem not ready" notification. In step 507, after obtaining the "subsystem not ready" notification, the respective software application SW1x prepares for termination, e.g. by completing all ongoing consequential activities that, if instantly stopped, may have consequences for the performance of the medical device when restarted after shutdown, i.e. by generating corrupt data, or jeopardize the health of the subject. Such consequential activities may include writing data to memory, completing a computation, generating a control signal for an actuator (17 in FIGS. 1A-1C), etc. The consequential activities may also relate to the user experience, e.g. completing playing an audio signal by the loudspeaker (15 in FIGS. 1A-1C), presenting a shutdown message on the display (12 in FIGS. 1A-1C), etc. Thus, in step 507, the respective software application may allow other activities, deemed non-consequential, to proceed for later termination. In step 508, when prepared for termination, the respective software application SW1x provides an "application ready for shutdown" notification. In step 509, manager SHM1 obtains the "application ready for shutdown" notifications from the software applications SW1. When the manager SHM1 has obtained "application ready for shutdown" notifications from all software applications SW1, the primary subsystem SS1 may be seen to be in state "subsystem not ready" (FIG. 6).

FIG. 5C is a flow chart of an embodiment of a method 503' for requesting termination of the software applications SW2-SW4 of the secondary subsystems SS2-SS4, which may be performed as part of step 503 in FIG. 5A. The method 503' is performed by each secondary subsystem SS2-SS4 separately. Steps 505-509 correspond to steps 505-509 of method 502' in FIG. 5B and will not be described further. It is understood that steps 505 and 509 are performed by the managers SHM2-SHM4, and that steps 506-508 are performed by the respective software application of the secondary subsystem SS2-SS4. After step 509, the respective secondary subsystem SS2-SS4 may be seen to be in state "subsystem not ready" (FIG. 6). In step 510, provided that the manager SHM2-SHM4 in step 509 has obtained the "application ready for shutdown" notification from all software applications of the respective secondary subsystem SS2-SS4, the respective manager SHM2-SHM4 provides a "subsystem ready for shutdown" notification for the primary subsystem SS1.

Reverting to FIG. 5A, in step 504, the manager SHM1 may initiate power loss only after obtaining the "subsystem ready for shutdown" notification from all secondary subsystems SS2-SS4 (generated by method 503') and after obtaining the "application ready for shutdown" notification from all software application SW1 in the primary subsystem SS1 (generated by method 502').

In a variant of step 504, it is conceivable that the manager SHM1 proceeds to initiate power loss also in the absence of the "subsystem ready for shutdown" notification from one or more of the secondary subsystems SS2-SS4, provided that a predefined time has elapsed since step 501. Thus, the manager SHM1 may set a timer that defines a maximum time delay until power loss is initiated. This mitigates the risk of a software freeze if a software application or hardware component malfunctions during shutdown. Similarly, it is conceivable that the managers SHM1-SHM4 set a corresponding timer in step 509 for obtaining the "application ready for shutdown" notifications.

It is also conceivable that one or more of the managers SHM1-SHM4, in step 509, completely disregards the "application ready for shutdown" notifications from one or more software applications, e.g. software applications for which all activities are inherently non-consequential if instantly stopped, or that such software application(s) do not provide an "application ready for shutdown" notification. For the same reason, it is also conceivable that the manager SHM1, in step 504, completely disregards the "subsystem ready for shutdown" notification from a subsystem, or that such a subsystem does not provide a "subsystem ready for shutdown" notification.

Each of the methods 502' and 503' ensures a deterministic shutdown of the respective subsystem SS1-SS4 and mitigates the risk of having ongoing consequential activities when power is cut.

In a further variant, only software applications in the secondary subsystems SS2-SS4 are configured to receive "subsystem not ready" notifications from their respective manager SHM2-SHM4 and provide "application ready for shutdown" notifications, whereas software applications in the primary subsystem SS1 are not.

While the methods 502' and/or 503' may serve to reduce health risks for the subject, there may be a need to further improve patient safety during shutdown of the medical device. In one embodiment, exemplified in FIG. 5D, a gatekeeping method 520 is performed by the software system before the primary subsystem SS1 is allowed to initiate shutdown in step 501. In the gatekeeping method 520, each critical software application is given a "veto power" to block shutdown of the software system if such a shutdown is deemed to impair patient safety. In step 521, after being notified about a shutdown command, the manager SHM1 of the primary subsystem SS1 proceeds to provide a "shutdown request" to the critical software applications, e.g. SW1c and SW3c in the example of FIG. 3. In step 522, each critical software application SW1c, SW3c validates the "shutdown request". In this validation, the respective critical software application SW1c, SW3c may assess whether a shutdown is acceptable based on or more predefined shutdown criteria. One such shutdown criterion may be patient safety. In one example, shutdown may be deemed unacceptable until the medical procedure, or a sub-procedure thereof, is completed. In another example, shutdown may be deemed unacceptable until a calibration procedure is completed. In another example, shutdown may be deemed unacceptable unless the critical software application is in a safe operating state, e.g. service mode, idle mode, etc. In step 523, the respective software application SW1c, SW3c provides an "application ready for shutdown" notification only if shutdown is deemed acceptable in step 522. Optionally, in step 524, the respective critical software application SW1c, SW3c may then enter a controlled state. In this context, a "controlled state" implies that the critical software application SW1c, SW3c operates in accordance with control parameter values that are set in view of patient safety, e.g. by reducing pump speed, stopping a pump, opening or closing a valve, turning off a heater, etc. The gatekeeping method 520 then proceeds to step 501, in which the manager SHM1 only proceeds to provide the "shutdown" notification if it has obtained the "application ready for shutdown" notification from all of the critical software applications SW1c, SW3c.

The gatekeeping method 520 prevents the medical device from being shut down unintentionally during ongoing medical procedure, e.g. by the operator pushing an on/off button. It may be noted that the above-mentioned timers are not implemented in the gatekeeping method 520, which means each critical software application has a true veto right over the shutdown process, which will be stopped at step 501 unless critical software applications provide "the application ready for shutdown" notification. In such a situation, it is conceivable that step 501 further involves asking the operator for confirmation that an override shutdown procedure should be initiated. If confirmed, the critical software applications may be set in the controlled state whereupon shutdown may proceed in accordance with the method 500 in FIG. 5A.

In the following, the above-described embodiments and further embodiments will be exemplified with reference to sequence diagrams in FIGS. 7A-7E and FIGS. 8A-8C. FIGS. 7A-7E depict sequences of steps performed during startup of a medical device, partitioned into methods for each of the transitions Ia, Ib, II and III in FIG. 6. FIGS. 8A-8C depict sequences of steps performed during shutdown of a medical device, partitioned into methods for each of the transitions IV, V and VI in FIG. 6. The illustrated sequences of steps presume that startup and shutdown occur without errors, although error handling will be briefly addressed in the following description.

Figure 6:
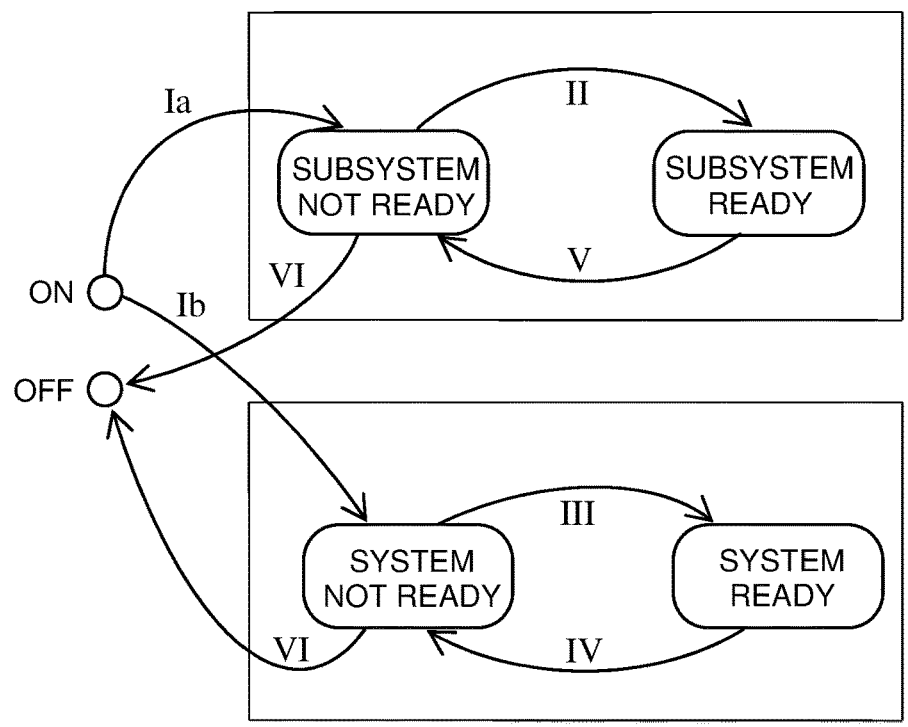
FIG. 6 illustrates the status of the software system in FIG. 3 when operated in accordance with embodiments of the invention.
Figure 7A:
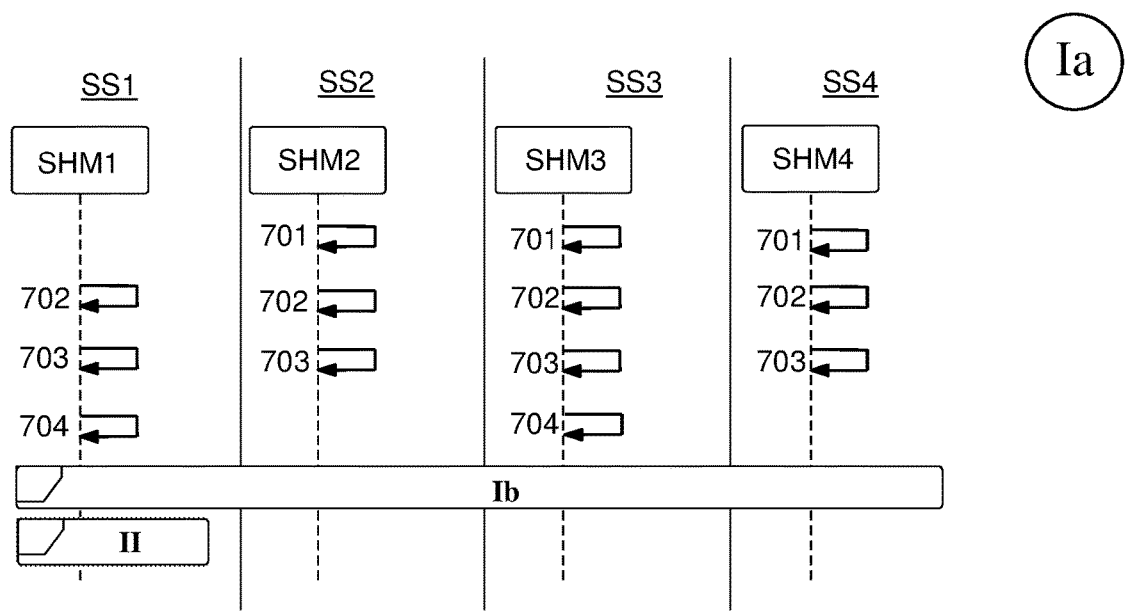
FIGS. 7A-7E are sequence diagrams of the operation of the software program in FIG. 3 for startup of a medical device in accordance with embodiments of the invention.

FIG. 7A depicts a method performed during subsystem initiation and corresponds to transition Ia in FIG. 6. The subsystem initiation in FIG. 7A presumes that a secure boot has been performed in SS1 and that SHM1 has checked the program binary for SS1. In step 701, during boot, SHM2, SHM3 and SHM4 check the respective program binary for SS2, SS3 and SS4, respectively. Should the check in step 701 fail for any of SS2-SS4, this will be detected by SS1 in subsequent step 712 (cf. FIG. 7B). In step 702, each of SHM1-SHM4 starts kicking a respective hardware watchdog, which means that a respective watchdog timer is restarted, as is well-known to the person skilled in the art. In step 703, SHM1-SHM4 identify software and hardware versions for SS1-SS4, respectively. In step 704, each of SHM1 and SHM3 sets a shutdown reason parameter to "Error" and stores it in non-volatile memory (cf. M1-M2 in FIG. 2). If a subsequent shutdown is performed without errors, the shutdown reason parameter is instead set to and stored as "Normal" (cf. step 826 in FIG. 8C). The reason for storing "Error" as default is to ensure that an erroneous shutdown in detected during startup. Thereby, even if the event of a rapid and unintentional shutdown, e.g. caused by power loss, the shutdown reason parameter will be stored as "Error". Step 704 may involve SHM1 and SHM3 performing an initial check of the stored value of the shutdown reason parameter. If the check by SHM1 (or SHM3) results in the value "Error", SHM1 (or SHM3, or both) may enter a recovery mode to enable SHM1 (or SHM3, or both) to recover from where they left off before the shutdown. In the illustrated example, step 704 is only performed by the critical subsystems, SS1 and SS3. However, it is conceivable that step 704 is performed also for SS2 and/or SS4, which do not include any critical software applications, to the extent that recovery of SS2 and/or SS4 is required or desirable.

After step 704, SS1-SS4 continue to transition Ib. As indicated in FIG. 7A, transition II for SS1 may be performed in parallel with transition Ib.

Figure 7B:
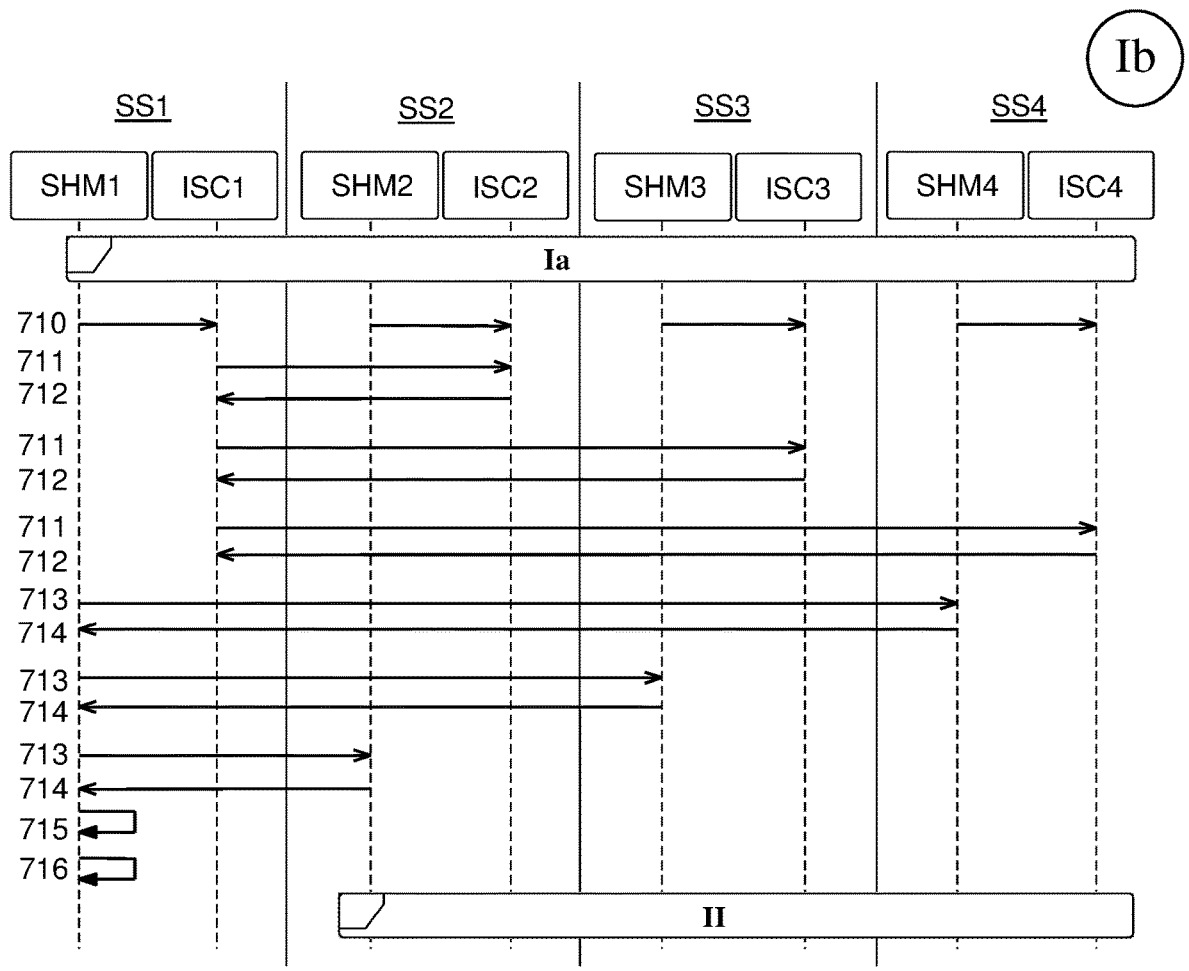
Figure 8A:
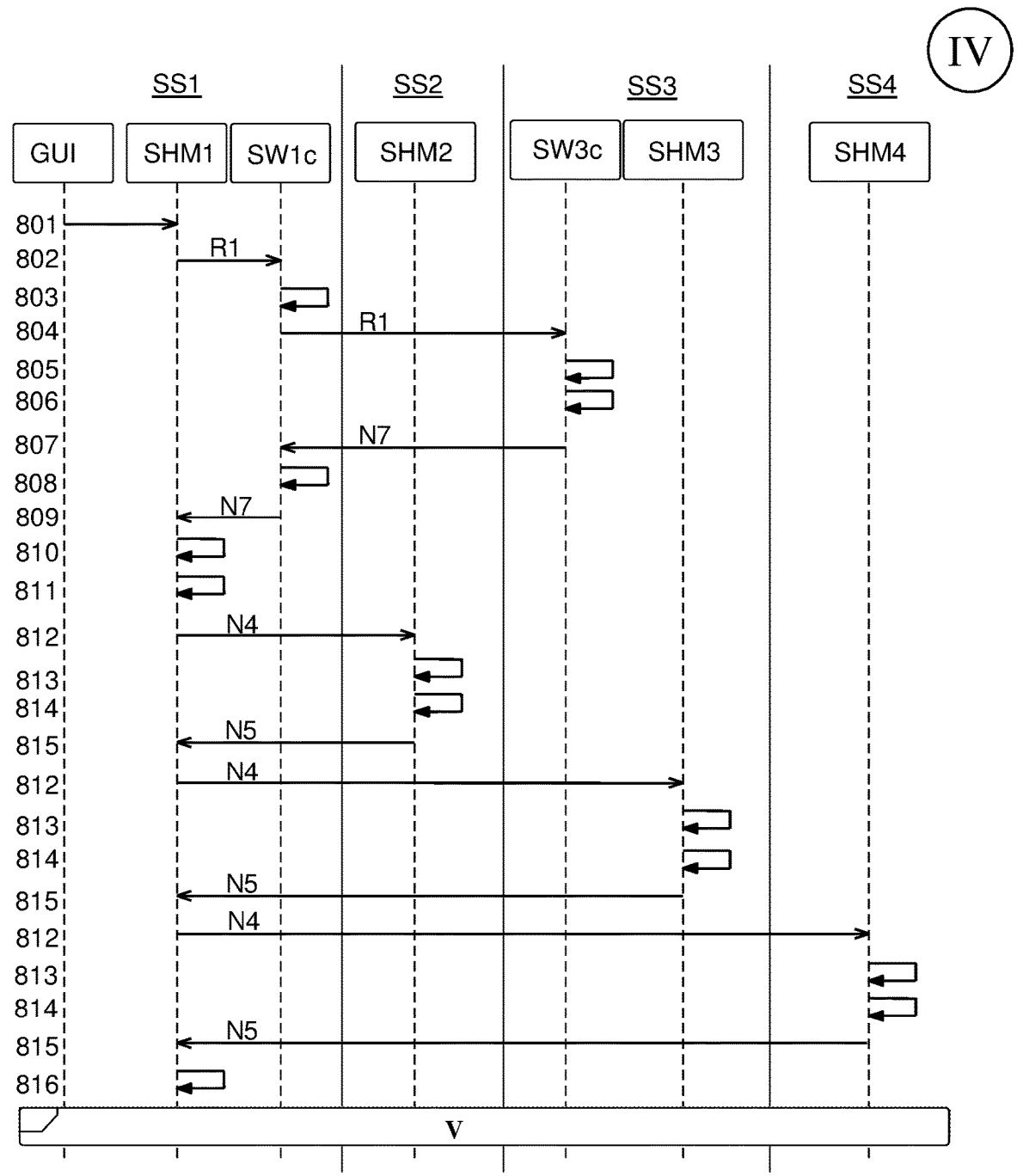
FIGS. 8A-8C are sequence diagrams of the operation of the software program in FIG. 3 for shutdown of a medical device in accordance with embodiments of the invention.
Figure 8B:
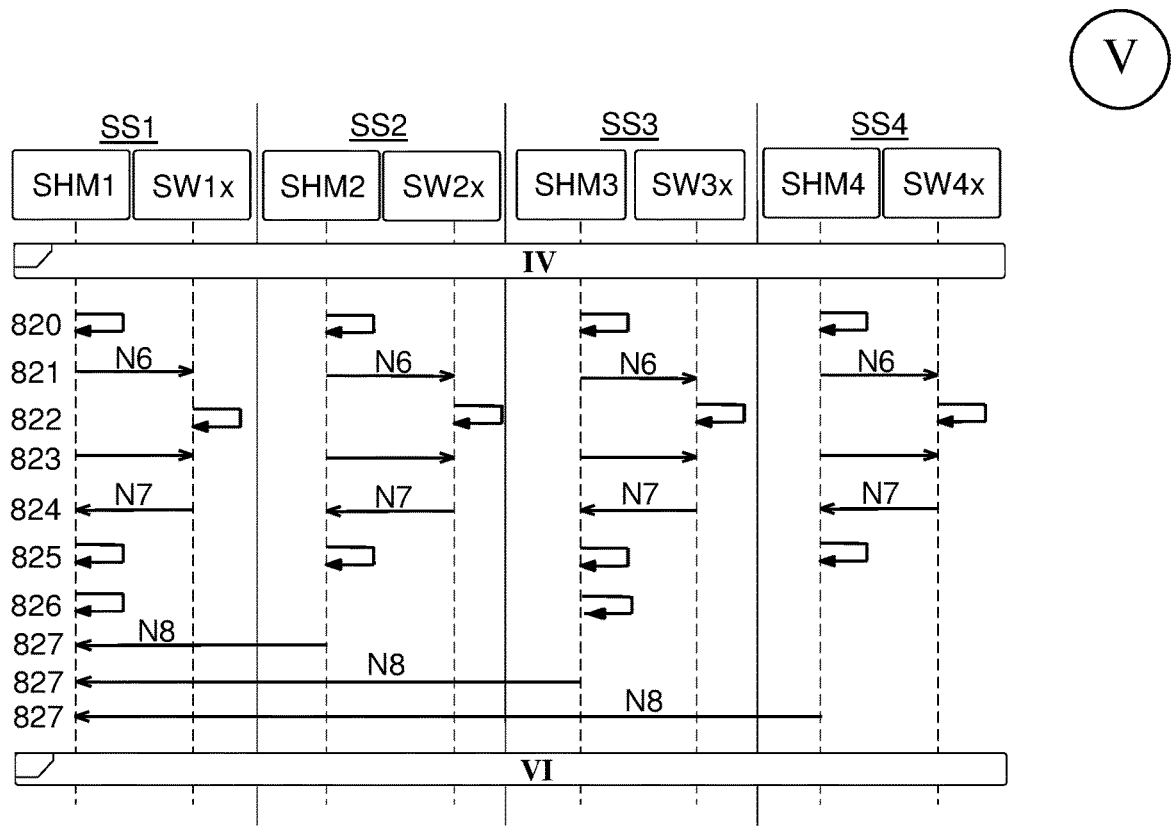
Figure 8C:
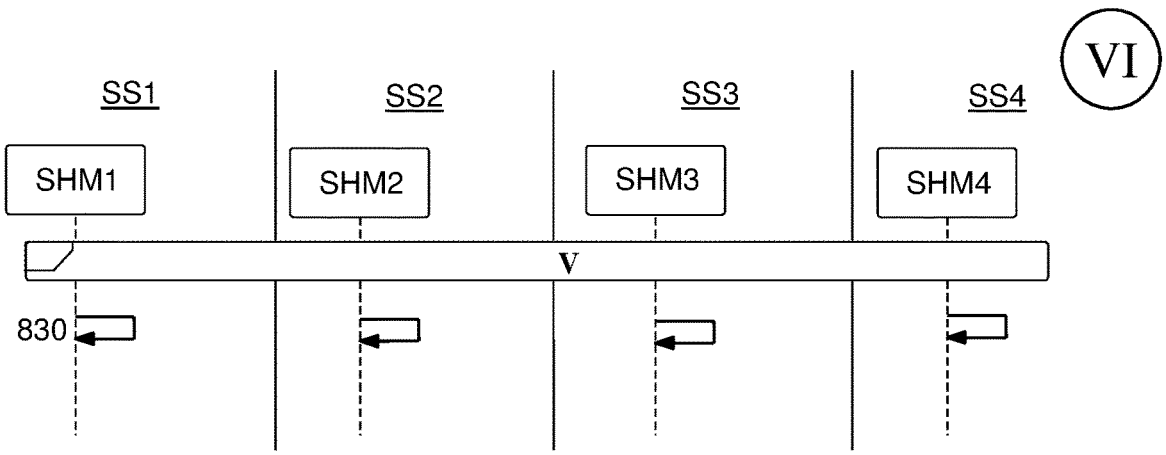

FIG. 7B depicts a method performed during system initiation and corresponds to transition Ib in FIG. 6. In step 710, SHM1-SHM4 start the respective communication module ISC1-ISC4 (cf. FIG. 3). SHM1 then repeatedly performs steps 711-712 to establish connection to each of SS2, SS3 and SS4, by providing a request for connection (step 711) and receiving a confirmation of established connection (step 712). If a connection cannot be established, ISC1 may report an error in the system. When connection is established, SHM1 repeatedly performs steps 713-714 to obtain software and hardware versions from SHM2, SHM3 and SHM 4, by providing a version request (step 713) and receiving version data. The version data may include identifiers of the respective software and hardware versions. If version data is not received, SHM1 may report an error in the system. When version data is received, SHM1 checks the software versions for compatibility with each other (step 715) and checks the software version for compatibility with the hardware version (step 716). For example, SHM1 checks the software versions of SS2, SS3 and SS4 for compatibility with the software version of SS1. If step 715 or step 716 fails, or both fail, SHM1 may report an error in the system.

After step 716, each of SS1-SS4 continues to transition II. As noted above, SS1 may perform transition II in parallel with transition Ib.

The methods in FIGS. 7A-7B serve to mitigate, e.g., a risk that the software versions in different subsystems are not compatible and/or that hardware and software do not match and/or that the program binary is corrupted in any one of SS2-SS4, all of which may result in an undefined behavior of the medical device.

The sequence diagrams in FIGS. 7A-7B may be seen to exemplify an embodiment in which a method for startup of a medical device comprises: starting the manager in each of the subsystems; starting, by the manager, a communication module in each of the subsystems (SS1-SS4); and establishing, by the communication module of the primary subsystem, a connection with the communication module in the respective secondary subsystem.

The sequence diagrams in FIGS. 7A-7B may also be seen to exemplify an embodiment in which a method for startup of a medical device comprises: obtaining, by the manager of the primary subsystem, software identifiers of software included the subsystems; and verifying, by the manager of the primary subsystem, compatibility of the software based on the software identifiers.

The sequence diagrams in FIGS. 7A-7B may also be seen to exemplify an embodiment in which a method for startup of a medical device comprises: obtaining, by the manager of the primary subsystem, hardware identifiers of hardware used by the subsystems; and verifying, by the manager of the primary subsystem, compatibility between hardware and software based on the hardware identifiers and software identifiers.

Figure 7C:
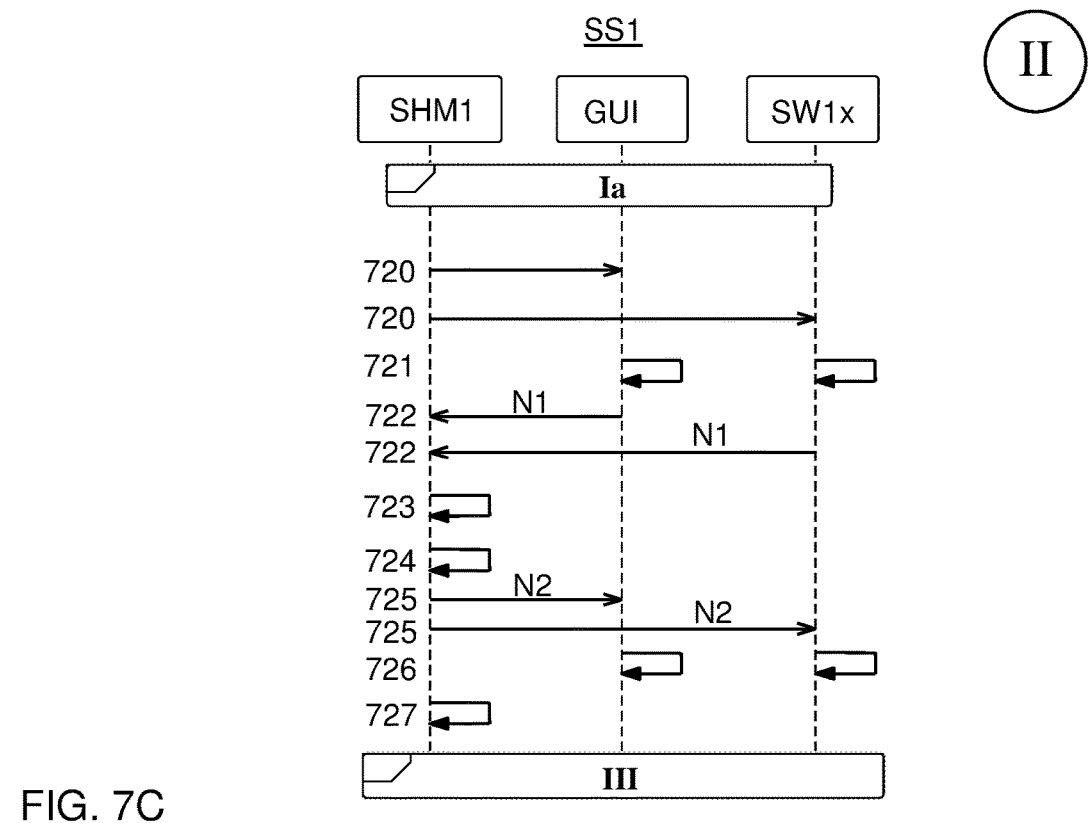

FIG. 7C depicts a method performed by SS1 during subsystem startup and corresponds to transition II in FIG. 6. In FIG. 7C, the individual software applications of SS1 are generally represented as SW1$x$. For the purpose of illustration only, FIG. 7C also explicitly depicts GUI, which is a software application responsible for graphical visualization on the display and for managing user input. GUI is preferably located in SS1 to ensure rapid commencement of user interaction. In step 720, SHM1 provides a start request to GUI and each SW1$x$ (cf. step 401). In step 721, after obtaining the start request, GUI and each SW1$x$ perform an internal startup. In some embodiments, the internal startup includes to prepare the software application for communication with other parts of the same subsystem, i.e. communication between software applications or processes within the same subsystem. In step 722, when ready for startup, GUI and each SW1$x$ provide a respective "application ready" notification, N1 (cf. step 402). This notification may indicate that the software application is ready for communication with other parts of the same subsystem. In step 723, SHM1 waits for N1 from GUI and each SW1$x$. If SHM1 does not receive N1 within a timeout period, SHM1 may report an error in the system. In step 724, SHM1 decides that GUI and each SW1$x$ are ready for startup, i.e. when they have provided "application ready" notifications. In step 725, SHM1 provides a "subsystem ready" notification, N2, to GUI and each SW1$x$ (cf. step 403). In step 726, after receiving N2, GUI and each SW1$x$ enable communication with each other within SS1 (cf. step 404). This means that any software application that is configured to exchange data with another software application in SS1 waits for N2 before starting the data exchange. However, other functionality of the respective software application may be activated before and/or after step 726. For example, GUI may be configured such that it enables user interaction as soon as possible upon step 726. However, in some embodiments, one or more (or all) of the software applications are configured to pause their internal startup after providing N1 and wait for N2 before continuing their internal startup. Further, GUI and each SW1$x$ are activated to send internal heartbeats within SS1, either before or after step 726, but in any event before step 727. In step 727, SHM1 starts monitoring the internal heartbeats within SS1, for ensuring that GUI and each SW1$x$ are operative. After step 727, SS1 is in state "subsystem ready" and continues to transition III.

Figure 7D:
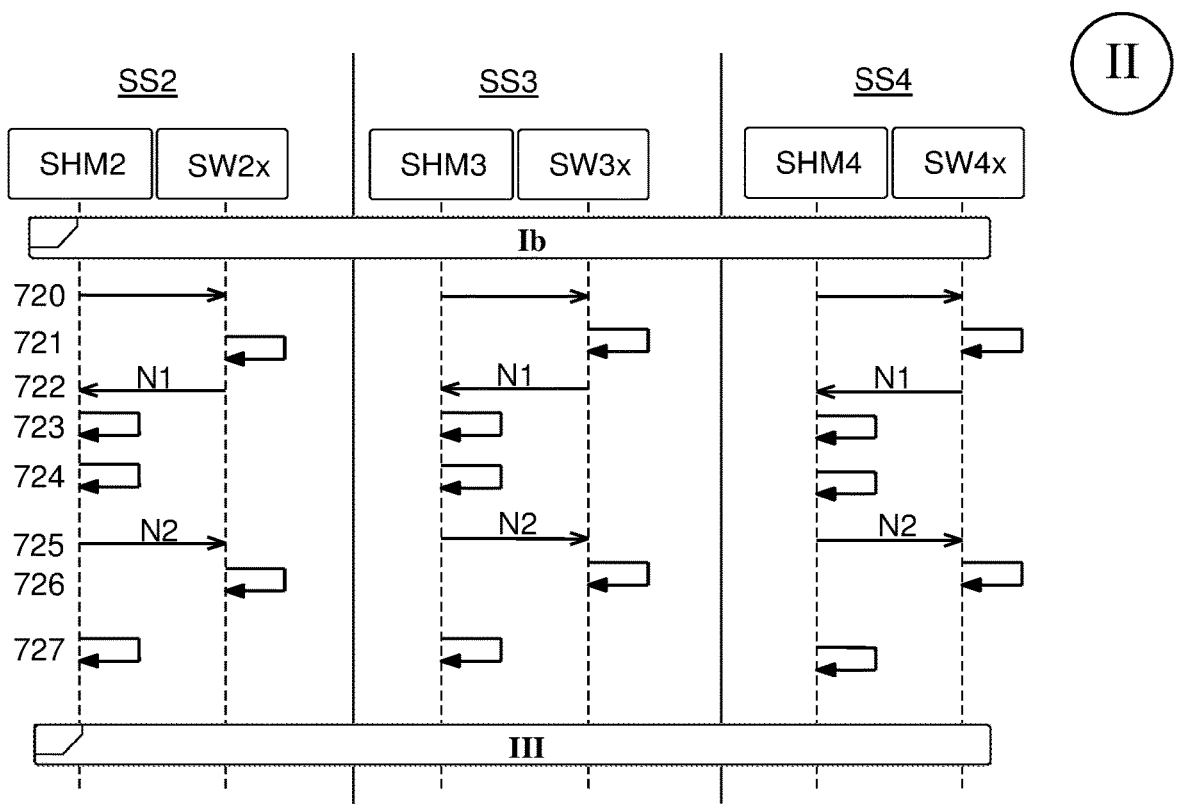

FIG. 7D depicts a method performed by SS2-SS4 during subsystem startup and corresponds to transition II in FIG. 6. In FIG. 7D, the individual software applications of SS2-SS4 are generally represented as SW2$x$-SW4$x$, respectively. The steps 720-727 in FIG. 7D corresponds to steps 720-727 in FIG. 7C, with the difference that they are performed within SS2-SS4 instead of SS1. Further, in some embodiments and in contrast to the method in FIG. 7C, SHM2-SHM4 may refrain from reporting an error in the system if N1 is not received within a timeout period. Instead, since absence of N1 implies that N2 is not generated, this error may be detected by SHM1 during system startup, specifically step 730 (cf. FIG. 7E). In view of the description of FIG. 7C, the subsystem startup in accordance with FIG. 7D should be self-explanatory and is not further described herein. After step 727, SS2-SS4 are in state "subsystem ready" and continues to transition III.

The methods in FIGS. 7C-7D serve to mitigate, e.g., a risk that a software application starts to communicate with another software application within a subsystem when the other software application is not ready for communication. In this situation, the other software application would be unable to receive or handle an incoming request, while the software application that communicates the request would be unaware of this inability.

The sequence diagrams in FIGS. 7C-7D may be seen to exemplify an embodiment in which a method for startup of a medical device, during the startup and for each subsystem, comprises: operating the software applications to send internal heartbeat signals; and starting to monitor, by the manager, the internal heartbeat signals for detection of operational failure of one or more of the software applications.

Figure 7E:
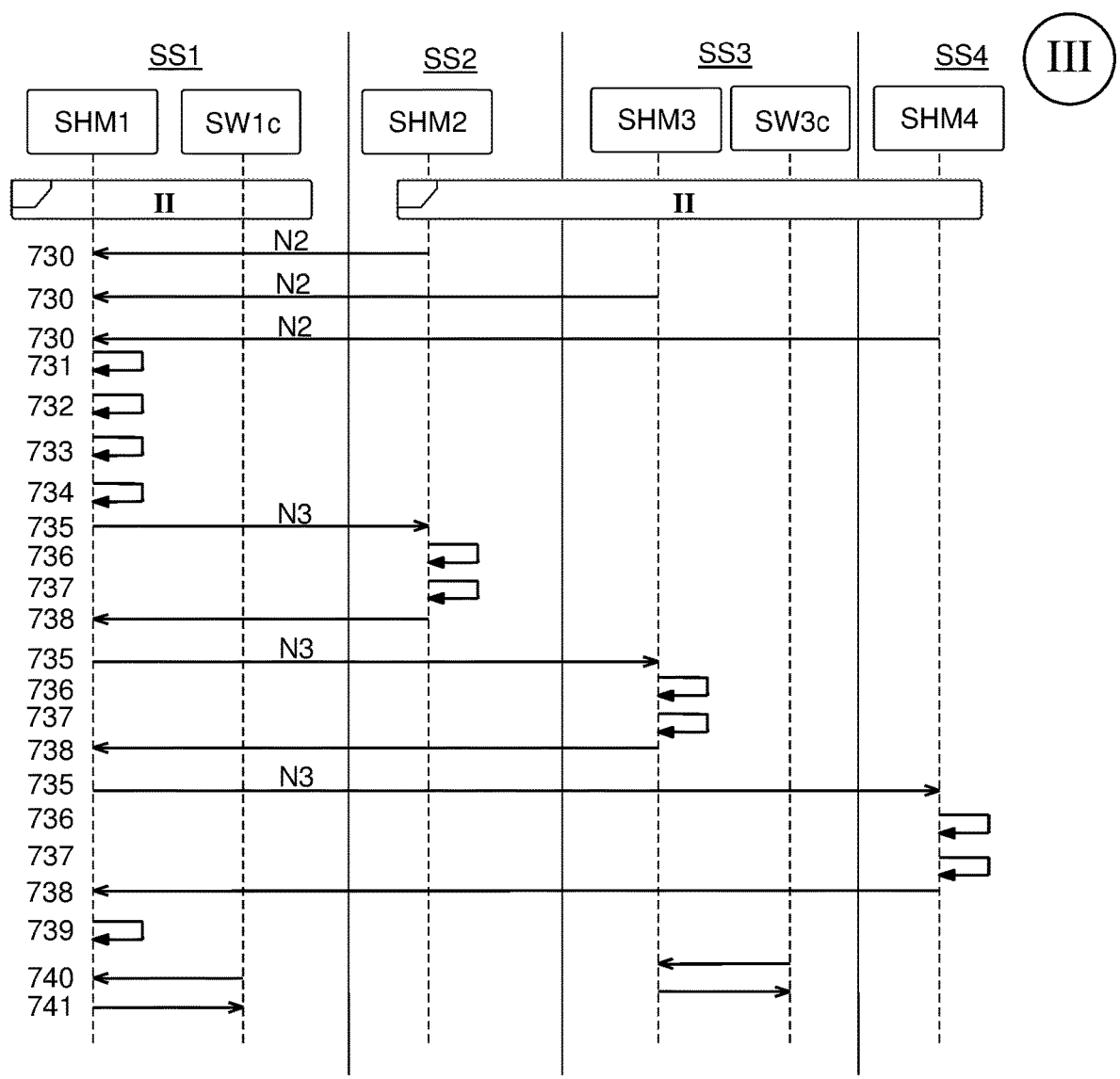

FIG. 7E depicts a method performed during system startup and corresponds to transition III in FIG. 6. In FIG. 7E, only SHM1-SHM4 and the critical software applications SW1c and SW3c are depicted, while any other software applications of SS1-SS4 are omitted. In step 730, when SS2-SS4 are ready, SHM1-SHM3 reports it to SHM1 by providing the "subsystem ready" notification, N2. In practice, step 730 may be replaced by step 725 in FIG. 7D, which thus provides N2 both internally and externally of the respective subsystem SS1-SS4. In step 731, SHM1 waits for N2 from all of SHM2-SHM4. If SHM1 does not receive N2 within a timeout period, SHM1 may report an error in the system. In step 732, SHM1 decides that all of SS1-SS4 are ready for startup (cf. step 405 in FIG. 4A). It may be noted that SHM1, at this stage, by default knows that SS1 is ready for startup since it has completed transition II in FIG. 7C. In step 733, SHM1 notifies all software applications in SS1 that the system is ready for startup. In step 734, SHM1 starts sending external heartbeats in the system. In step 735, SHM1 provides a "system ready" notification, N3, for receipt by SHM2-SHM4 (cf. step 406 in FIG. 4B). In step 736, after obtaining N3 (cf. step 407 in FIG. 4B), each of SHM2-SHM4 notifies all of its software applications of status "system ready". In step 737, each of SHM2-SHM4 starts sending external heartbeats in the system. In step 738, each of SHM2-SHM4 provides a confirmation notification for receipt by SHM1. If SHM1 does not receive the confirmation notification within a timeout period, SHM1 may report an error in the system. In step 739, after receiving the confirmation notification from all of SHM2-SHM4, SHM1 starts monitoring external heartbeats in the system. At any time after step 737, the software applications in each of SS1-SS4 are allowed to start application-level communication with software applications in one or more other subsystems (cf. step 408 in FIG. 4B), on the established communication paths between SS1-SS4 (cf. FIG. 3).

The example in FIG. 7E further includes steps 740-741, which are only performed in relation to the critical software applications, SW1c and SW3c and which need to be completed before each of SW1c and SW3c are allowed to communicate with software applications in other subsystems. In step 740, SW1c/SW3c requests a confirmation from SHM1/SHM3 of the "system ready" status. In step 741, SHM1/SHM3 confirms the status to SWc1/SW3c. This provides an additional level of robustness against malfunctions that may impair patient safety.

To provide a further level of robustness, it is conceivable that step 737 in the critical subsystem SS3 also involves SHM3 starting to monitor external heartbeats generated by the other critical subsystem SHM1. Thereby, mutual monitoring of heartbeats is established between the critical subsystems SS1, SS3, enabling subsystem to rapidly detect an operational failure in the other critical subsystem and take appropriate action.

The method in FIG. 7E serves to mitigate, e.g., a risk that a first software application in one subsystem starts to communicate with a second software application in another subsystem when the latter is not ready for communication. In this situation, the second software application would be unable to receive or handle an incoming request, and the first software application would be unaware of the problem at the receiving end.

The sequence diagram in FIG. 7E may be seen to exemplify an embodiment in which a method for startup of a medical device comprises: operating the manager of the respective secondary subsystem to send external heartbeat signals; and starting to monitor, by the manager of the primary subsystem, the external heartbeat signals for detection of operational failure of one or more of the secondary systems.

The sequence diagram in FIG. 7E may also be seen to exemplify an embodiment in which a method for startup of a medical device comprises: operating each of the managers of two or more critical subsystems to send external heartbeat signals; and starting to monitor, mutually among the managers of the critical subsystems, the external heartbeat signals for detection of an operational failure.

Further, the sequence diagrams in FIGS. 7C-7E may be seen to exemplify an embodiment in which a method for startup of a medical device, during the startup, comprises: reporting a first error, by the manager in the primary subsystem, when the "application ready" notification, N1, is not received from the software applications of the primary subsystem within a first predefined time period; and reporting a second error, by the manager in the primary subsystem, when the "subsystem ready" notification, N2, is not received from the secondary subsystems within a second predefined time period.

FIG. 8A depicts a method performed during system shutdown and corresponds to transition IV in FIG. 6. At the onset of the method, it is assumed that the software system is up and running and thus is in status "system ready" in FIG. 6. The illustrated example also presumes that SW3c has been registered as a "Shutdown Gatekeeper" to SHM1 and is thereby a subscriber to "shutdown" requests. In step 801, the operator enters a command to shut down the medical device, e.g. by pressing a control button. The command is detected by GUI, which provides a shutdown request for receipt by SHM1. In step 802, SHM1 forwards the shutdown request, R1, for receipt by SW1c. In step 803, SW1c validates R1. In step 804, after successful validation, SW1c provides R1 to SW3c. In step 805, SW3c validates R1. After successful validation, SW3c enters a controlled state (step 806) and provides an "application ready for shutdown" notification, N7, for receipt by SW1c (step 807). After receiving N7, SW1c enters a controlled state (step 808) and forwards N7 to SHM1 (step 809). After receiving N7, SHM1 proceeds with system shutdown. If the validation fails in step 803 and/or if SHM1 does not receive N7 in step 809 within a timeout period, SHM1 may return a "shutdown not approved" notification to GUI, which may then inform the operator accordingly.

Figure 5D:
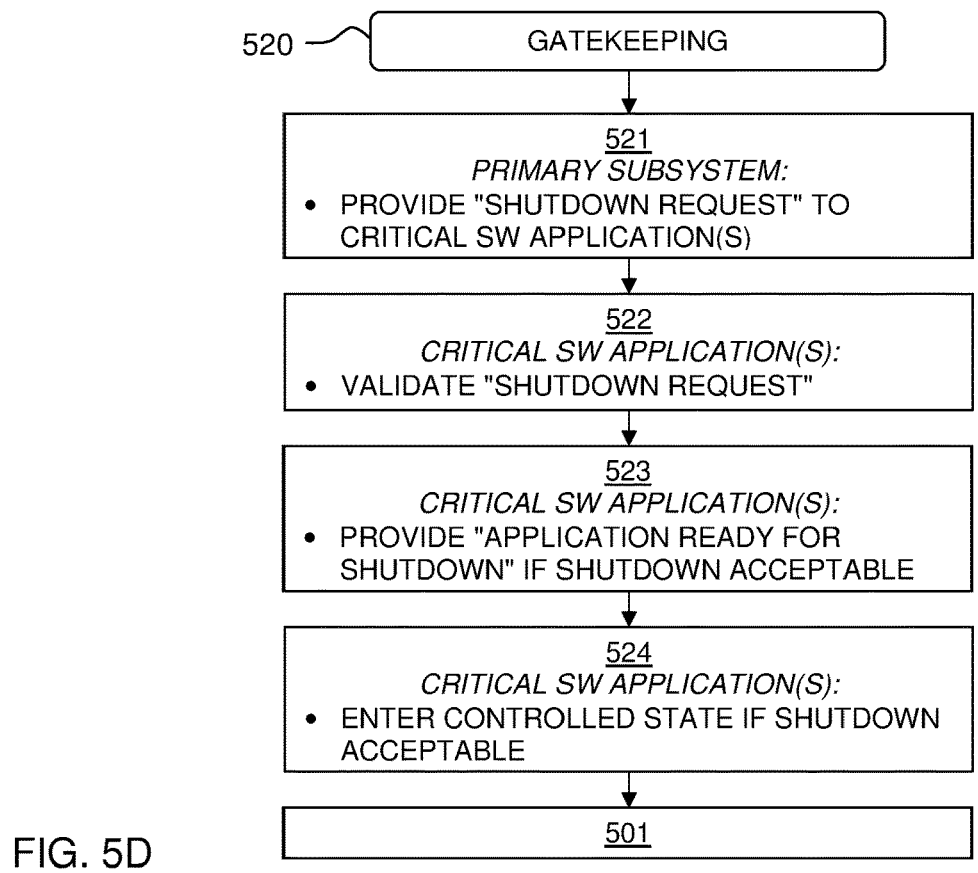

The combination of steps 802-809 corresponds to the gatekeeping method 520 of FIG. 5D and shows that neither R1, nor N7, need to be provided in direct communication between SHM1 and the respective critical software application SW1c, SW3c, but may be relayed in a chain of transmissions. Thus, when comparing FIG. 5D and FIG. 8A, step 521 may correspond to steps 802 and 804, step 522 may correspond to steps 803 and 805, step 523 may correspond to steps 807 and 809, and step 524 may correspond to steps 806 and 808. In a variant, N7 is not relayed in the chain of transmission but is directly provided from SW3c to SHM1.

In step 810, SHM1 updates its status to "system not ready" by stopping application-level communication with SS2-SS4. In step 811, SHM1 stops monitoring external heartbeats, i.e. heartbeats generated by SS2-SS4. In step 812, SHM1 provides a "shutdown" notification, N4, for receipt by SHM2-SHM4 (cf. step 501 in FIG. 5A). In step 813, after receiving N4, each of SHM2-SHM4 updates its status to "system not ready" by stopping application-level communication with the other subsystems. In step 814, each of SHM2-SHM4 stops sending external heartbeats. If the software system implements the above-described mutual heartbeat monitoring between critical subsystems, step 814 in SS3 may also cause SHM3 to stop monitoring external heartbeats generated by SHM1. In step 815, after completion of steps 813-814, each of SHM2-SHM4 provides a "confirmation" notification, N5, for receipt by SHM1. N5 signals to SHM1 that the respective subsystem SS2-SS4 has received N4. In step 816, after receiving N5, SHM1 stops sending external heartbeats. If SHM1 does not receive N5 from all of SS2-SS4 within a timeout period, SHM1 may report an error in the system.

The method in FIG. 8A serves to mitigate, e.g., a risk that the medical device is shut down on operator initiative while the medical device is performing the medical procedure, in particular when an interruption of the medical procedure might impair patient safety, as well as the risk that one critical subsystem or software application prepares for termination while another critical subsystem or software application does not. For example, patient safety would be jeopardized if the above-mentioned protective system goes down while the medical procedure is continued.

The sequence diagram in FIG. 8A may be seen to exemplify an embodiment in which a method for shutdown of a medical device comprises, before providing the "shutdown" notification N4 to the secondary subsystem(s): providing, by the manager of the primary subsystem, a shutdown request R1 for a first critical software application in a chain of critical software applications, thereby causing each of the critical software applications in the chain to validate the shutdown request R1 in view of the operation of the medical device and provide, if shutdown is acceptable, the shutdown request R1 for a subsequent critical software application in the chain, until the shutdown request R1 is received by a final critical software application in the chain; wherein the final critical software application in the chain validates the shutdown request R1 in view of the operation of the medical device and causes, if shutdown is acceptable, an "application ready for shutdown" notification N7 to be provided for the manager of the primary subsystem. Such a conditional and sequential validation of the shutdown request R1 may serve to improve the robustness of the gatekeeping method.

The sequence diagram in FIG. 8A may also be seen to exemplify an embodiment in which a method for shutdown of a medical device, wherein the "application ready for shutdown" notification N7 is relayed along the chain of critical software applications to the manager of the primary subsystem.

The sequence diagram in FIG. 8A may also be seen to exemplify an embodiment in which each of the critical software applications in the chain enters, upon receiving the "application ready for shutdown" notification N7, a controlled state in which the medical device is operated in accordance with a predefined set of parameter values.

FIG. 8B depicts a method performed during subsystem shutdown and corresponds to transition V in FIG. 6. The method in FIG. 8B may be performed by each of SS1-SS4 at any time after receiving the "shutdown" notification, N4 (step 812 in FIG. 8A). In step 820, each SHM1-SHM4 stops monitoring internal heartbeats. In step 821, each of SHM1-SHM4 provides a "subsystem not ready" notification, N6, for its software applications (cf. step 505 in FIGS. 5B-5C). In step 822, after receiving N6, the software applications prepare for termination and stop communication among each other within the respective subsystem (cf. steps 506-507 in FIGS. 5B-5C). In step 824, when prepared for termination, the respective software application SW1$x$-SW4$x$ provides an "application ready for shutdown" notification, N7, for its manager SHM1-SHM4 (cf. step 508 in FIG. 5B-5C). Optionally, as indicated by step 823 in FIG. 8B, N7 may be sent in response to a confirmation request from the managers SHM1-SHM4. In step 825, each of SHM1-SHM4 waits for N7 from all of its software applications. If any one of SHM1-SHM4 does not receive N7 from all of its software applications within a timeout period, it may report an error in the system. In step 826, after completion of step 825, SHM1 and SHM3 in the critical subsystems SS1, SS3 sets the shutdown reason parameter to "Normal" and stores it in non-volatile memory. In step 827, each of SHM2-SHM4 provides a "subsystem ready for shutdown", N8, for SHM1 (cf. step 510 in FIG. 5C). The software system is now prepared, both on system level and subsystem level, for a power loss.

The method in FIG. 8B serves to mitigate, e.g., a risk that power is cut when a software application performs a consequential activity, as exemplified above with reference to FIGS. 5B-5C.

The sequence diagrams in FIG. 7A and FIG. 8B may be seen to exemplify an embodiment in which a method of operating a medical device comprises: setting, in absence of errors during shutdown and by at least one of the managers, a shutdown reason parameter to indicate normal shutdown and storing the shutdown reason parameter in a set of memory units. Further, the method may comprise: setting, during startup and by the at least one of the managers, the shutdown reason parameter to indicate a shutdown error and storing the shutdown reason parameter in the set of memory units.

FIG. 8C depicts a method performed during execution exit of the software system and corresponds to transition VI in FIG. 6. The method in FIG. 8C is performed by each of SS1-SS4 after completion of step 827. In step 830, each of SHM1-SHM4 waits for power loss while continuing to kick a respective hardware watchdog. It is not possible for any of SS1-SS4 to leave this state without a power loss. At this stage, the system may be safely shut down. For example, SHM1 may in step 830 cause the medical device to cut the power, e.g. by generating a "power-cut" notification for a power manager of the medical device.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:

1. A method of operating a medical device configured to perform a medical procedure, the medical device including a set of processors and a set of memory units storing a software system for execution by the set of processors, the software system defining a plurality of subsystems including a primary subsystem and a set of secondary subsystems, wherein each subsystem comprises software applications that are involved in the operation of the medical device during the medical procedure, and wherein two or more subsystems are critical to the medical procedure performed by the medical device and each comprise a respective manager, said method comprising, during startup of the medical device:
- initiating each of the software applications;
- providing, by each of the software applications in the respective secondary subsystem when ready for startup, an application ready notification;
- providing, by the respective secondary subsystem when all of its software applications have provided the application ready notification, a subsystem ready notification;
- coordinating, by the primary subsystem upon receiving the subsystem ready notification, startup of the set of secondary subsystems;
- operating each of the managers of said two or more subsystems to send external heartbeat signals; and
- initiating a monitoring of, mutually among the managers of said two or more subsystems, the external heartbeat signals for detection of an operational failure.

2. The method of claim 1, comprising, during shutdown of the medical device:
- providing, by the manager of the primary subsystem, a shutdown notification for the set of secondary subsystems;
- requesting, by the manager of the primary subsystem, termination of the software applications of the primary subsystem; and
- requesting, by the manager of the respective secondary subsystem after obtaining the shutdown notification, termination of the software applications of the respective secondary subsystem.

3. The method of claim 2, wherein said requesting termination of the software applications of the respective secondary subsystem comprises, for at least one secondary subsystem:
- providing, by the manager, a subsystem not ready notification for the software applications of the secondary subsystem;
- preparing for termination, by at least a subset of the software applications of the secondary subsystem upon obtaining the subsystem not ready notification;
- providing, by said at least a subset of the software applications when prepared for termination, an application ready for shutdown notification; and
- providing, by the manager of the secondary subsystem upon obtaining the application ready for shutdown notification from said at least a subset of the software applications, a subsystem ready for shutdown notification for the manager of the primary subsystem.

4. The method of claim 3, wherein said requesting termination of the software applications of the primary subsystem comprises:
- providing, by the manager of the primary subsystem, a subsystem not ready notification for the software applications of the primary subsystem;
- preparing for termination, by at least a subset of the software applications of the primary subsystem upon obtaining the subsystem not ready notification; and
- providing, by said at least a subset of the software applications of the primary subsystem when prepared for termination, an application ready for shutdown notification.

5. The method of claim 4, further comprising: initiating power loss of the medical device, by the manager of the primary subsystem upon obtaining the subsystem ready for shutdown notification from said at least one secondary subsystem and the application ready for shutdown notification from said at least a subset of the software applications of the primary subsystem.

6. The method of claim 2, further comprising:
- setting, in absence of errors during said shutdown and by at least one of the managers, a shutdown reason parameter to indicate normal shutdown and storing the shutdown reason parameter in the set of memory units; and
- setting, during said startup and by said at least one of the managers, the shutdown reason parameter to indicate a shutdown error and storing the shutdown reason parameter in the set of memory units.

7. The method of claim 2, wherein the software applications comprise one or more critical software applications, which are critical to the medical procedure performed by the medical device, said method further comprising, during shutdown of the medical device and before providing the shutdown notification for the set of secondary subsystems:
- providing, by the manager of the primary subsystem, a shutdown request for the one or more critical software applications;
- validating, by the one or more critical software applications, the shutdown request in view of the operation of the medical device; and
- providing, by at least one of the one or more critical software applications and if shutdown is acceptable, an application ready for shutdown notification,
- wherein the manager of the primary subsystem, upon obtaining the application ready for shutdown notification from said at least one of the one or more critical software applications, provides the shutdown notification for the set of secondary subsystems.

8. The method of claim 1, wherein the manager of the respective secondary subsystem provides the subsystem ready notification upon obtaining the application ready notification from all of its software applications.

9. The method of claim 8, wherein said coordinating comprises: providing, by the manager of the primary subsystem upon obtaining the application ready notification from each of the software applications of the primary subsystem and the subsystem ready notification from the respective secondary subsystem, a system ready notification for the respective secondary subsystem.

10. The method of claim 9, further comprising:
- enabling, by the manager of the respective secondary subsystem upon obtaining the system ready notification and by the manager of the primary subsystem, communication between at least a subset of the software applications of different subsystems among the plurality of subsystems, whereupon the medical device is ready to perform at least part of the medical procedure.

11. The method of claim 10, wherein the software system defines at least two secondary subsystems, and wherein said enabling communication between at least the subset of the software applications comprises: enabling direct communication between at least a software application in each of the at least two secondary subsystems.

12. The method of claim 1, further comprising: providing, by a respective software application in the primary subsystem when ready for startup, the application ready notification, wherein said coordinating is performed by the primary subsystem upon receiving the subsystem ready notification from the respective secondary subsystem and the application ready notification from the respective software application in the primary subsystem.

13. The method of claim 12, wherein the manager in the primary subsystem receives the subsystem ready notification from the respective secondary subsystem and the application ready notification from the respective software application in the primary subsystem and performs said coordinating.

14. The method of claim 13, further comprising, during said startup:
reporting a first error, by the manager in the primary subsystem, when the application ready notification is not received from the respective software application of the primary subsystem within a first predefined time period; and
reporting a second error, by the manager in the primary subsystem, when the subsystem ready notification is not received from the respective secondary subsystem within a second predefined time period.

15. The method of claim 1 wherein said coordinating comprises: generating, by the primary subsystem, a system ready notification for receipt by the set of secondary subsystems.

16. The method of claim 15, wherein said coordinating further comprises: enabling, by the respective secondary subsystem upon obtaining the system ready notification, communication between at least a subset of the software applications of different subsystems among the plurality of subsystems, whereupon the medical device is ready to perform at least part of the medical procedure.

17. The method of claim 1, wherein the plurality of subsystems comprises:
a first subsystem with a software application for controlling the medical device to perform the medical procedure, and
a second subsystem with a software application for communicating with an actuator and/or a sensor of the medical device,
wherein said coordinating enables communication between the software application for controlling the medical device and the software application for communicating with the actuator and/or the sensor.

18. The method of claim 17, wherein the plurality of subsystems further comprises:
a third subsystem with a software application for detecting deviations in the medical procedure, and
a fourth subsystem with a software application for communicating with an auxiliary sensor of the medical device,
wherein said coordinating further enables communication between the software application for detecting deviations in the medical procedure and the software application for communicating with the auxiliary sensor, and between the software application for controlling the medical device and the software application for detecting deviations in the medical procedure.

19. The method of claim 1, further comprising: enabling, in the respective secondary subsystem including the software applications of the respective secondary subsystem upon obtaining the subsystem ready notification, communication between the software applications of the respective secondary subsystem.

20. The method of claim 1, wherein each of the subsystems is executed on a separate processor in the set of processors.

21. A medical device for performing a medical procedure, the medical device comprising:
a set of processors; and
a set of memory units storing a software system for execution by the set of processors,
wherein the software system, when executed by the set of processors, operates the medical device to perform the medical procedure,
wherein the software system defines a plurality of subsystems, including a primary subsystem and a set of secondary subsystems, wherein each subsystem comprises software applications that are involved in the operation of the medical device during the medical procedure,
wherein two or more subsystems are critical to the medical procedure performed by the medical device and each comprise a respective manager, and
wherein the software system, when executed by the set of processors, causes the set of processors to:
initiate each of the software applications;
provide, via each of the software applications in the respective secondary subsystem when ready for startup, an application ready notification;
provide, via the respective secondary subsystem when all of its software applications have provided the application ready notification, a subsystem ready notification;
coordinate, via the primary subsystem upon receiving the subsystem ready notification, startup of the set of secondary subsystems;
operate each of the managers of said two or more subsystems to send external heartbeat signals; and
initiate a monitoring of, mutually among the managers of said two or more subsystems, the external heartbeat signals for detection of an operational failure.

22. A non-transitory, computer-readable medium comprising a software system for operating a medical device to perform a medical procedure, said software system defining a plurality of subsystems, including a primary subsystem and a set of secondary subsystems, wherein each subsystem comprises software applications that are involved in the operation of the medical device during the medical procedure, wherein two or more subsystems are critical to the medical procedure performed by the medical device and each comprise a respective manager, and wherein the software system, when executed by a set of processors of the medical device, causes the set of processor to:
initiate each of the software applications;
provide, via each of the software applications in the respective secondary subsystem when ready for startup, an application ready notification;
provide, via the respective secondary subsystem when all of its software applications have provided the application ready notification, a subsystem ready notification;
coordinate, via the primary subsystem upon receiving the subsystem ready notification, startup of the set of secondary subsystems;
operate each of the managers of said two or more subsystems to send external heartbeat signals; and
initiate a monitoring of, mutually among the managers of said two or more subsystems, the external heartbeat signals for detection of an operational failure.

* * * * *